(12) United States Patent
Sun et al.

(10) Patent No.: US 8,318,943 B1
(45) Date of Patent: Nov. 27, 2012

(54) SORBITOL/DEXLANSOPRAZOLE CO-CRYSTALS AND METHOD FOR MAKING SAME

(75) Inventors: Tong Sun, Marlton, NJ (US); Shawn Watson, Cherry Hill, NJ (US)

(73) Assignee: Takeda Pharmaceuticals U.S.A., Inc. DE (US)

( * ) Notice: Subject to any disclaimer, the term of this patent is extended or adjusted under 35 U.S.C. 154(b) by 274 days.

(21) Appl. No.: 12/662,422

(22) Filed: Apr. 16, 2010

(51) Int. Cl.
*C07D 401/12* (2006.01)

(52) U.S. Cl. .................................................. 546/273.7

(58) Field of Classification Search ............... 546/273.7
See application file for complete search history.

(56) References Cited

U.S. PATENT DOCUMENTS

2010/0204479 A1* 8/2010 Vladiskovic et al. ...... 546/273.7
* cited by examiner

*Primary Examiner* — Patricia Morris
(74) *Attorney, Agent, or Firm* — Cooley LLP

(57) ABSTRACT

A crystal of dexlansoprazole and sorbitol. The crystal is a co-crystal or a salt thereof of dexlansoprazole and sorbitol. There is also a method for making the co-crystal or salt thereof.

23 Claims, 29 Drawing Sheets

(1 of 29 Drawing Sheet(s) Filed in Color)

SORBITOL/DEXLANSOPRAZOLE CO-CRYSTALS AND METHOD FOR MAKING SAME

BACKGROUND OF THE INVENTION

1. Field of the Invention

The present disclosure relates to crystals of co-crystals and salts or polymorphic forms thereof having a co-crystal former and an active pharmaceutical ingredient. The present disclosure further relates to crystals of co-crystals and salts or polymorphic forms thereof having sorbitol and dexlansoprazole. The present disclosure still further relates to methods for making the co-crystals and salts or polymorphic forms thereof.

2. Description of the Related Art

Co-crystals and salts thereof are crystals of two or more components. Whether the crystal is in co-crystal form or salt form is determined by the location of the proton between an acid and a base. For acid-base complexes with similar pKa values, the extent of proton transfer in the solid state is not predictable and a continuum exists between the two extremes.

Co-crystals and their salts typically contain one or more active pharmaceutical ingredients (APIs). They typically contain one or more APIs and one or more formers that form crystals. The formers can take any form of matter, such as a solid, liquid, or gas, and can have neutral or ionic species.

Co-crystals and their salts can be manufactured by a variety of techniques, such as fast and slow evaporation of API/former solutions, sonication of supersaturated solutions, grinding, and melting, i.e., Kofler technique, and reaction crystallization. The selection of technique may vary depending on factors such as physical and chemical properties of the former(s), physical and chemical properties of the APIs, and manufacturing scale.

Co-crystals and their salts are useful forms for making, processing, or delivering active APIs. They are useful, for example, to optimize API stability, enhance API bioavailability, enhance manufacturing efficiency, modulate physical properties, and provide flexibility in regulatory compliance.

Teachings to co-crystals and their salts, their physicochemical properties, and methods for making are disclosed in *Pharmaceutical Cocrystals and Their Physicochemical Properties* by Schultheiss and Newman, Crystal Growth & Design 2009, vol. 9, no. 6, pp. 2950 to 2967, which is incorporated herein by reference in its entirety.

Dexlansoprazole is the pure enantiomer of lansoprazole. Dexlansoprazole and lansoprazole are APIs used for drug products that inhibit gastric acid secretion. They are useful in the treatment and maintenance of patients with erosive oesophagitis and non-erosive reflux disease, i.e. gastro-oesophageal reflux disease.

It would be desirable to have dexlansoprazole available in a co-crystal/salt form for patient administration. It would be desirable to have dexlansoprazole available in a co-crystal/salt form for inhibition of gastric acid secretion.

SUMMARY OF THE INVENTION

According to the present disclosure, there is provided a crystal. The crystal is a co-crystal, a salt or a polymorphic form thereof of dexlansoprazole and sorbitol.

Further according to the present disclosure, there is provided a method for making a co-crystal, a salt or a polymorphic form thereof. The method has the steps of (a) mixing dexlansoprazole and sorbitol in an amount of one or more solvents effective to yield a substantially homogeneously dispersed solution, and (b) evaporating the one or more solvents from the solution.

DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Dexlansoprazole is the pure enantiomer of lansoprazole. Lansoprazole is an important active pharmaceutical ingredients used for drug products to inhibit gastric acid secretion. Dexlansoprazole and potential co-crystals/salts thereof may be referred to in laboratory tests herein associated with the nomenclature "SP134".

The general formula of dexlansoprazole is $C_{16}H_{14}F_3N_3O_2S$. Dexlansoprazole has a molecular weight of 369.36. The structural formula is the following:

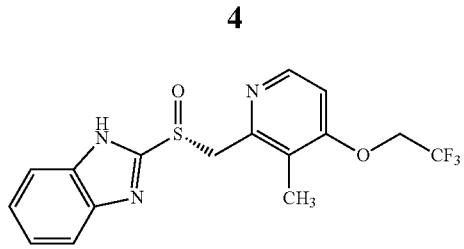

Dexlansoprazole is a white to nearly white crystalline powder that melts with decomposition at 140° C. Dexlansoprazole is freely soluble in dimethyl formamide, methanol, dichloromethane, ethanol, and ethyl acetate. Dexlansoprazole is soluble in acetonitrile, slightly soluble in ether, very slightly soluble in water, and substantially insoluble in hexane. Dexlansoprazole is stable when exposed to light. Dexlansoprazole is more stable in neutral and alkaline conditions than acidic conditions.

The co-crystal former, D-sorbitol, or also D-glucitol, is a sugar alcohol with the molecular formula $C_6H_{14}O_6$. The structural formula for sorbitol is the following:

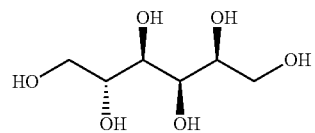

The crystal of the present invention preferably has dexlansoprazole and sorbitol present at a molar ratio ranging from about 1:1 to about 1:2, from about 1:1 to about 1:1.8, from about 1:1 to about 1:1.5, from about 1:1 to about 1:1.4, about 1:1, or about 1:1.5 in the form of a co-crystal and/or salt thereof.

Figure 22:
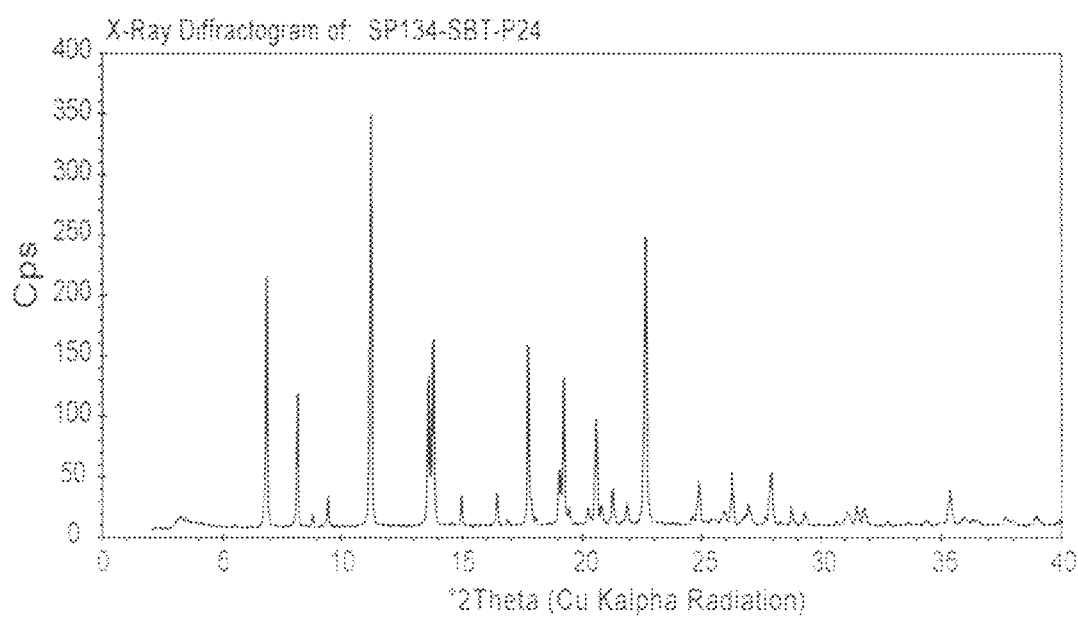
FIG. 22 is the PXRD (powder X-ray diffractogram) pattern of SP134-SBT-P24 (1:1 dexlansoprazole-sorbitol co-crystal).

The crystal of 1:1.5 dexlansoprazole-sorbitol co-crystal of the invention may be characterized by an X-ray powder diffraction (XRPD) pattern with 2-Theta angles at peaks of 5.30 and 17.83 degrees and preferably 5.30, 5.85, 10.64, 17.83, and 18.09 degrees. The crystal also is characterized by Raman spectra peaks at 1268.45 $cm^{-1}$ and 1406.35 $cm^{-1}$ and preferably 121.87 $cm^{-1}$, 607.24 $cm^{-1}$, 1003.53 $cm^{-1}$, 1268.45 $cm^{-1}$, and 1406.35 $cm^{-1}$. The crystal of 1:1 dexlansoprazole-sorbitol co-crystal of the invention may be characterized by XRPD patterns depicted in FIG. 22.

Dexlansoprazole and the sorbitol are present in the crystal in a mole proportion at least 90 mole percent thereof, preferably at least 95 mole percent thereof, and most preferably at least 99 mole percent thereof based on the total number of moles in the crystal.

The co-crystal and/or salt thereof can be made or formed by any technique known in the art. Two effective techniques are evaporation and combined suspension equilibration/evaporation.

In the first formation technique, the dexlansoprazole and sorbitol are mixed, dispersed, or dissolved in an amount of one or more solvents effective to yield a substantially homogeneously mixture. The mixture can take the form of a dispersion, suspension, or solution as desired. The solution form is preferred. The solvent(s) is then evaporated from the mixture to yield a substantially crystalline residue.

In the second formation technique, the mixture is agitated for an extended period of time and the solvent(s) is then evaporated. The period of agitation can be for a time sufficient to enhance the degree of homogeneity of the dexlansoprazole and sorbitol in the mixture. A preferred period of time is 24 hours or more. A more preferred period of time is 48 hours or more. A most preferred period of time is 72 hours or more.

Evaporation of the solvent(s) is preferably carried out under an inert gas, such as nitrogen. Evaporation may take place at any temperature and pressure but is conveniently carried out at room temperature (ambient temperature) at atmospheric pressure. Evaporation at elevated temperatures and at reduced pressure is feasible and within the scope of the disclosure.

The present invention further provides a method for making a co-crystal or salt thereof, comprising the steps of: (a) dissolving sorbitol in one or more solvents to form a sorbitol solution; (b) adjusting temperature of the sorbitol solution to about 40° C.; (c) dissolving dexlansoprazole in one or more solvents to form a dexlansoprazole solution; (d) adding the dexlansoprazole solution to the sorbitol solution to form a mixture at a temperature ranging from about 40° C. to about 45° C.; (e) cooling the mixture to a temperature ranging from about 2° C. to about 10° C.; (f) stirring the mixture at a temperature ranging from about 2° C. to about 10° C. for a period of time ranging from about 30 minutes to about 25 hours; and (g) recovering the co-crystal or salt thereof which precipitates from the mixture in step (f). Step (c) can be carried out concurrently with or before step (b) or step (a).

The one or more solvents may contain ethanol (EtOH), DMSO, ethyl acetate (EtOAc), tetrahydrofuran (THF), acrylonitrile (MeCN), acetonitrile, methanol (MeOH), tert-butyl methyl ether (TBME) or combination thereof. For example, the solvents may comprise DMSO/EtOH (1:5, v/v). Step (a) can be carried out at any suitable temperature so as to form a sorbitol solution, e.g., at an ambient temperature, or at an ambient temperature followed by heating to a temperature ranging from about 40° C. to about 60° C. Step (e) may be carried out at a cooling rate ranging from about 0.05 K/min to about 0.5 K/min, from about 0.1 K/min to about 0.3 K/min, from about 0.1 K/min to about 0.2 K/min, about 0.1 K/min, or about 0.2 K/min. Seeding crystals in a suspension may be added to the mixture before step (e). The period of time in step (f) may be at least about 5 hours, at least about 10 hours, or at least about 15 hours. The co-crystal or salt thereof may be recovered in step (g) by any suitable method in the art, such as vacuum filtration.

As used herein, the term "ambient temperature" means a temperature ranging from about 12° C. to about 28° C., from about 15° C. to about 25° C., from about 18° C. to about 22° C., about 20° C., or about 25° C.

The following are examples of the present disclosure and are not to be construed as limiting.

EXAMPLES

Example 1

Summary of Results

A screening for co-crystals of dexlansoprazole was performed with sorbitol (SBT).

The co-crystal screening was performed in a micro-titer plate by evaporation of mixed stock solutions from four solvents (ethanol, ethyl acetate, acetonitrile and THF) followed by suspension equilibration of the solid residues in four solvent systems (ethanol/heptane 1:1, ethyl acetate, TBME and acetonitrile/$H_2O$ 9:1).

A good lead for co-crystal formation was obtained for the sorbitol (SBT) co-crystal former.

Crystallization optimization and scale-up crystallization experiments were carried with sorbitol (SBT) as co-crystal former. Quick-screen results were reproduced and the sorbitol co-crystal characterized by FT-Raman spectroscopy, x-ray powder diffraction (XRPD), $^1$H nuclear magnetic resonance spectroscopy ($^1$H-NMR), TG-FTIR, differential scanning calorimetry (DSC), dynamic vapor sorption (DVS), elemental composition analysis, and aqueous solubility measurements.

The XRPD confirmed the crystallinity of the sample. The $^1$H-NMR and the elemental composition analysis were consistent with the 1:1.5 ratio of free drug to co-crystal former. No decomposition or solvent residues was observed. The TG-FTIR showed no mass loss at 25° C.-170° C. and decomposition>170° C. In the DSC, a sharp peak was seen at 160° C. ($\Delta H$=120.6 J/g), possibly attributable to melting. In the DVS, a total gain of ~20 wt % at a relative humidity of 95% was observed. The weight gain and loss was reversible. The sample was hygroscopic (gain of ~7 wt % at 85% relative humidity).

TG-FTIR was carried out in a Netzsch Thermo-Microbalance TG 209 with Bruker FT-IR Spectrometer Vector 22 with an aluminum crucible (with microhole), a $N_2$ atmosphere, a 10 K/m in heating rate, a 25-250° C. or a 25-350° C. range.

DSC was carried out in a Perkin Elmer DSC 7. The instrument was employed with closed gold crucibles, a sample filled and equilibrated for 3 minutes under $N_2$, a 10 K/min heating rate, a −50 to 200° C. range, and two heating scans with quench cooling (200 K/min) to −50° C. inbetween.

DVS was carried out in a Surface Measurement System DVS-1. The sample was placed on a platinum holder on top of a microbalance and allowed to equilibrate for 2 hours at 50% r.h. before starting the pre-defined humidity program: 50→95% r.h. (5%/h); 5 hours at 95% r.h., 95→0% r.h. (5%/h); 5 h at 0% r.h., then 0→50% r.h. (5%/h); and 2 hours at 50% r.h.

The hygroscopicity was classified based on the mass gain at 85% r.h. relative to the initial mass as follows: deliquescent (sufficient water adsorbed to form a liquid), very hygroscopic (mass increase of ≧15%), hygroscopic (mass increase <15% but ≧2%), slightly hygroscopic (mass increase <2% but ≧0.2%), or non-hygroscopic (mass increase <0.2%).

Elemental analysis was carried out in a Leco CHN 800 for C, H, and N determination by combustion. The analysis was carried out in a Leco RO-478 for determination of O by pyrolysis. A homebuilt apparatus was used for F combustion followed by quantitative reductive conversion to fluoride and potentiometric detection using a Metrohm or Orion ion meter.

The dexlansoprazole/sorbitol co-crystal was stable as a solid. The co-crystal was not stable in water for 24 hours (at 25° C.) as disintegration into its components was observed (sorbitol being more soluble in water than solid dexlansoprazole precipitate).

The solubility of the dexlansoprazole/sorbitol co-crystal was measured as a function of time. After 15 minutes, a constant value of 0.25 mg/ml was reached.

Characterization of the Starting Material

A sample of dexlansoprazole sesquihydrate was characterized by FT-Raman spectroscopy, XRPD, $^1$H-NMR and approximate solubility tests.

FT-Raman spectroscopy was carried out on a Bruker RFS100 with OPUS 3.1 software, Nd:YAG laser with 1064-nm excitation, Ge detector, 3500-100 $cm^{-1}$ range, and conventional measurement conditions of 100-300 mW laser power, 64-128 scans, and 2 $cm^{-1}$ resolution.

Figure 1:
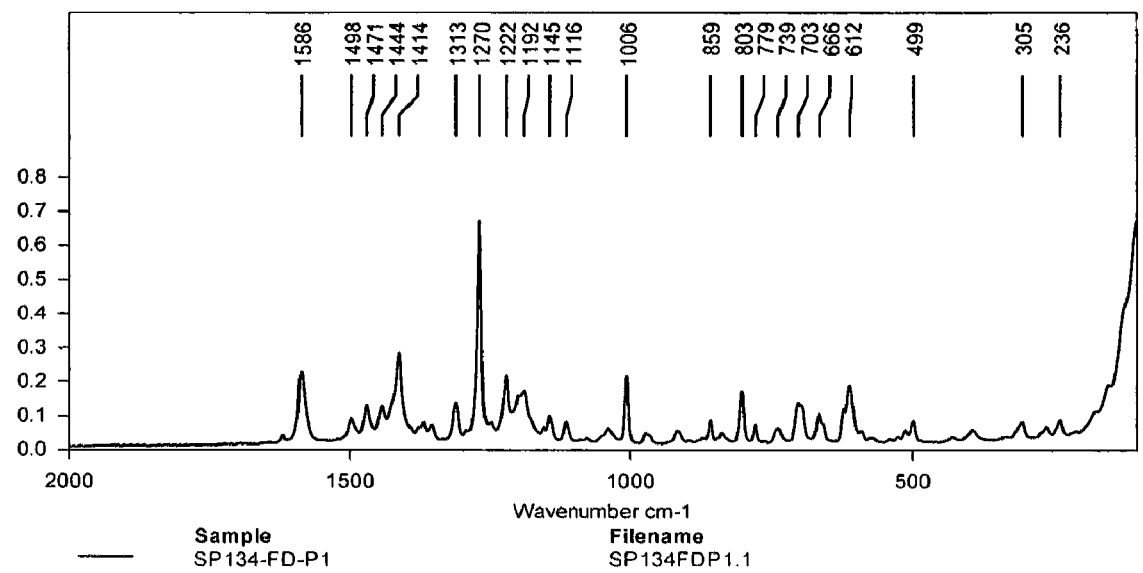
FIG. 1 is a plot of a Raman spectrum of dexlansoprazole sesquihydrate drug substance (SP134-FD-P1).

The FT-Raman spectrum of dexlansoprazole is shown in FIG. 1 and used as the reference pattern for the free drug form. The most important peaks are labeled in the Figure and there are only two significant peaks at 3072 and 2942 $cm^{-1}$ that are not shown here.

XPRD was carried out of a Bruker D8 Advance with Cu—Kα radiation, a LynxEye detector with 3° window and standard measurement conditions of 40 kV/40 mA tube power, a variable divergence slit, a diffracted beam Ni-filter, a 0.02° 2θ step size, a 37 second step time, 2.5°-50° 2θ scanning range. The samples were generally measured without any special treatment other than the application of slight pressure to get a flat surface. Ambient air atmosphere was used. A silicon single crystal sample holder of 0.1 mm deep with 5 mg to 20 mg sample amount was used. The samples were rotated (0.5 rps) during measurement. The d-value Analysis was performed with software EVA from Bruker, version 14,0,0,0; Cu Kalpha2 was removed by software; only lines up to 35° 2θ are listed. Calculation of relative intensity was with a formula in Excel.

Figure 2:
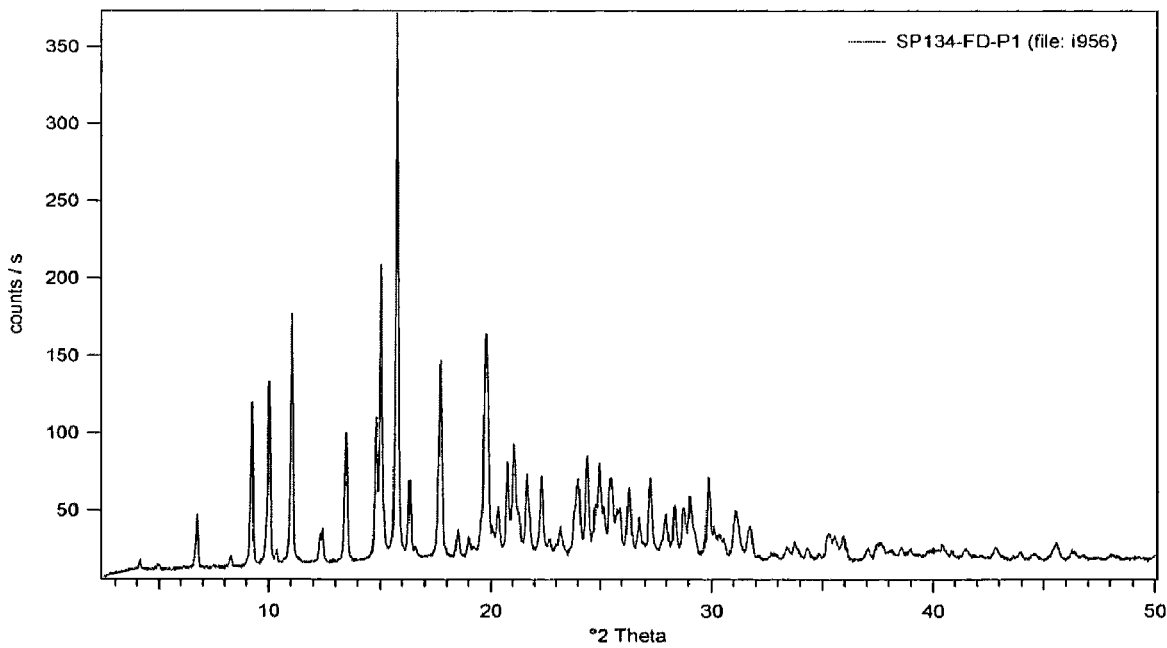
FIG. 2 is a plot of an x-ray powder diffraction (XRPD) pattern of the dexlansoprazole sesquihydrate drug substance (SP134-FD-P1).

The XRPD pattern of the dexlansoprazole drug substance SP134-FD-P1 confirmed the crystallinity of the material and is used as reference pattern for the free drug form. The XRPD pattern is shown in FIG. 2.

Figure 3:
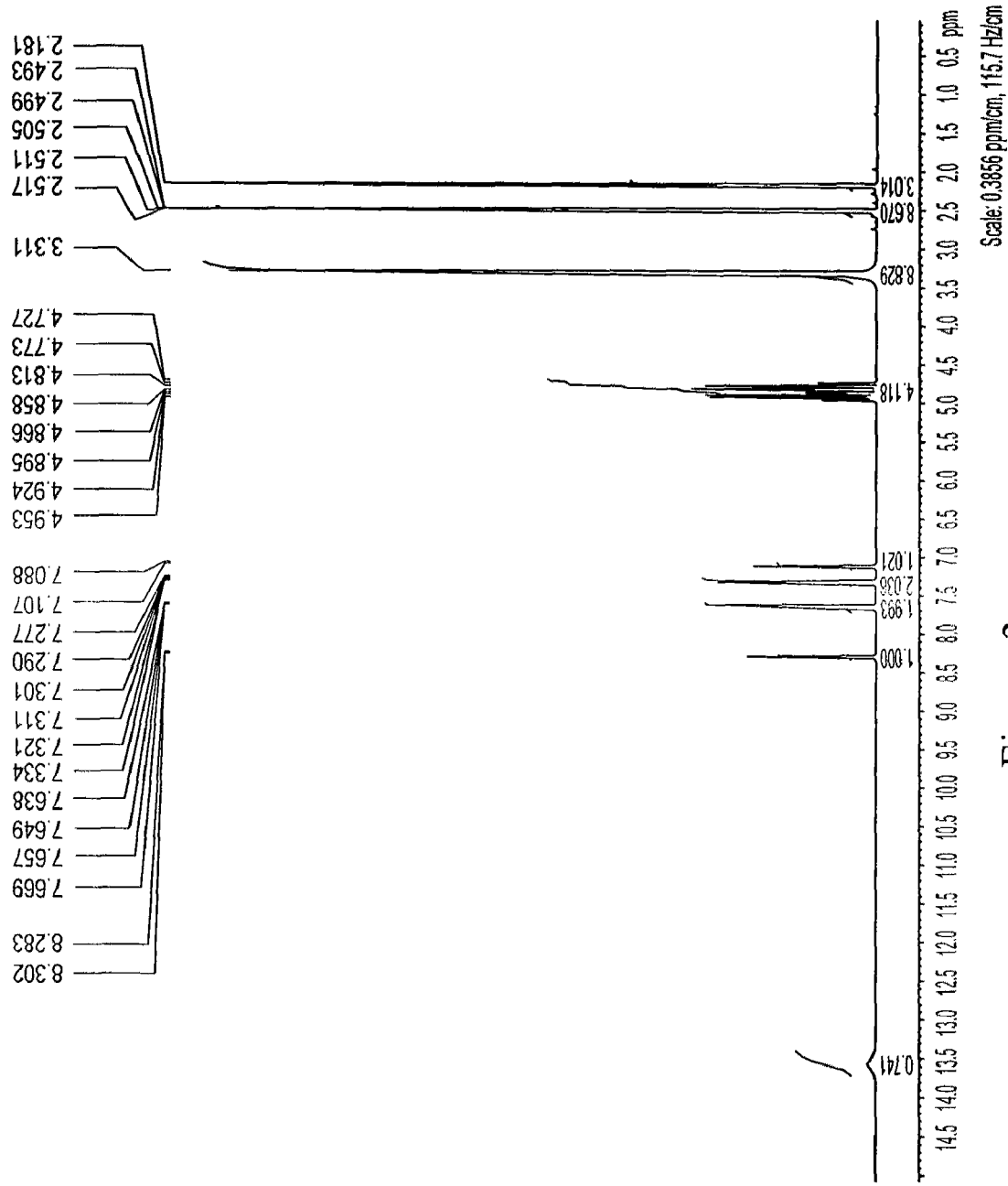
FIG. 3 is a plot of a $^1$H-NMR ($^1$H nuclear magnetic resonance spectroscopy) spectrum of the dexlansoprazole sesquihydrate drug substance (SP134-FD-P1).

$^1$H-NMR was carried out on a Bruker DPX300 spectrometer at a proton frequency of 300.13 MHz, a 30° excitation pulse, a recycle delay of 1 second at 300.13 MHz, and an accumulation of 16 scans, and DMSO as solvent. The $^1$H-NMR spectrum is shown in FIG. 3.

The $^1$H-NMR spectrum was consistent with the structure.

HPLC was carried out in a TSP instrument with a P4000 pump, an AS3000 autosampler, an SCM1000 degasser, a UV3000 detector, and PC1000 Version 4.1 software. The method is set forth in Table 1 below.

TABLE 1

(General HPLC method used for solubility determinations)

| Column | Waters, Xterra MS C18, 4.6 × 100 mm, 5 μm (CC01) | | |
|---|---|---|---|
| Mobile Phase A | $H_2O$/MeCN 95:5 + 0.1% TFA | | |
| Mobile Phase B | $H_2O$/MeCN 5:95 + 0.1% TFA | | |
| Reference conc. | ca. 0.1 mg/mL | | |
| Retention time | 8.0 min | | |
| Gradient | 0.0 min | 100% A | 0% B |
|  | 20 min | 0% A | 100% B |
|  | 21 min | 100% A | 0% B |
|  | 30 min | 100% A | 0% B |
| Flow | 1.0 mL/min | | |
| Injection Volume | 10 μL | | |
| Wavelength | 280 nm | | |

Solubility was determined by adding approximately 0.5 mL of doubly distilled water to 19.1 mg of the substance to be measured. The resulting suspension was equilibrated in a temperature-controlled Eppendorf Thermomixer Comfort Shaker for 24 hours at 25° C. at a shaking rate of 500 rpm. The solid phase was recovered by filter centrifugation (0.1-μm PVDF membrane) and examined by FT-Raman spectroscopy. Concentrations in the filtrate (i.e., saturated solutions) or diluted solutions thereof were determined using the HPLC method disclosed herein. The pH of the saturated solution was determined with a Metrohm 713 pH meter.

The obtained solubility data along with publicly available information confirmed that dexlansoprazole is sufficiently soluble in many typical organic solvents. The data are presented in Table 2. Solvents selected for the evaporation experiment of the co-crystal screening preferably demonstrated good solubility. Accordingly, ethanol, ethyl acetate, acetonitrile, and THF were chosen as solvents for the co-crystal screening.

TABLE 2

(Results of Approximate Solubility Tests in Selected Solvents)

| Solvent | Solubility [S, mg/ml] |
|---|---|
| Acetone | ~230 |
| Acetonitrile | ~210 |
| Dichloromethane | ~99 < S < 198 |
| Ethanol | ~228 |
| Ethyl acetate | ~204 |
| Methanol | ~204 |
| MEK | ~226 |
| THF | ~228 |

Experimental Set-Up and Co-Crystal Screening Procedure

Crystallization experiments with the sorbitol were performed in a 96-well quartz micro titer plate. Two experiments were carried out: 1) An evaporation experiment (SP134-X-P1 and SP134-X-P3), and 2) a combined suspension-equilibration/evaporation experiment (SP134-X-P2 and SP134-X-P4).

In the evaporation experiments (SP134-X-P1 and SP134-X-P3), the sorbitol was screened in four solvents. Stock solutions of the sorbitol were prepared in ethanol (EtOH), ethyl acetate (EtOAc), tetrahydrofuran (THF) and acrylonitrile (MeCN) (mostly in concentrations of 0.05 mol/l). The microtiter plate setup was designed so that mixing of stock solutions of sorbitol led to a 200 μl solution with 1:1 ratios (stoichiometric amounts) of free drug and sorbitol in each well. The solvents were evaporated under controlled $N_2$ flow (~0.4 l/h). Raman spectra and microscopic images were collected of each solid residue.

For the suspension equilibration experiments (SP134-X-P2 and SP134-X-P4) EtOH/heptane (1:1), EtOAc, tert-butyl methyl ether (TBME), and MeCN/$H_2O$ (9:1) were chosen as solvents and solvent mixtures.

For the combined suspension equilibration/evaporation experiment, the wells were filled with 100 μl solvent: EtOH/heptane (1:1), EtOAc, TBME, or MeCN/$H_2O$ (9:1). For phase equilibration (slurry), the microtiter plate was shaken (500 rpm) for three days at room temperature. The solvents were again evaporated under controlled $N_2$ flow (~0.4 l/h). Raman spectra and microscopic images were collected of each residue.

Co-Crystal Screening Results

The samples obtained from the quick-screen experiments SP134-X-P1 to SP134-X-P4 were analyzed visually, by optical microscopy, and by Raman spectroscopy.

For optical microscopy, Leitz Orthoplan 110680 microscope equipped with a Leica DFC280 camera and IM50 v.5 image-capturing software were used. Images were recorded with or without crossed polarizers and with 4×, 10× or 25× magnification.

Raman spectra and microscopic images were collected of each solid residue after each experiment. The Raman spectra were evaluated by comparing them with the spectra of the corresponding co-crystal former, the relevant solvents, and the known form of the free drug.

The combination of optical and spectroscopic analysis provides reasonably good indications for successful co-crystal formation. Microscopic analysis should reveal birefringent material and the obtained Raman spectra should be consistent with formation of a co-crystal.

Summary of Screening Results

New and promising Raman spectra distinctive for a co-crystal former were obtained for sorbitol (SBT).

Figure 4:
FIG. 4 depicts a microscopic image (with crossed polarizers) taken from well F3 showing crystalline material.
Figure 5:
FIG. 5 depicts a microscopic image (with crossed polarizers) taken from well F6 showing possibly a sorbitol co-crystal.

Images of very clearly crystalline materials with a Raman spectrum from more than one solvent system were observed for the sorbitol co-crystal former (FIGS. 4 and 5). A possible sorbitol co-crystal was found in wells P3-F6, F9, and P4-F3.

Figure 6:
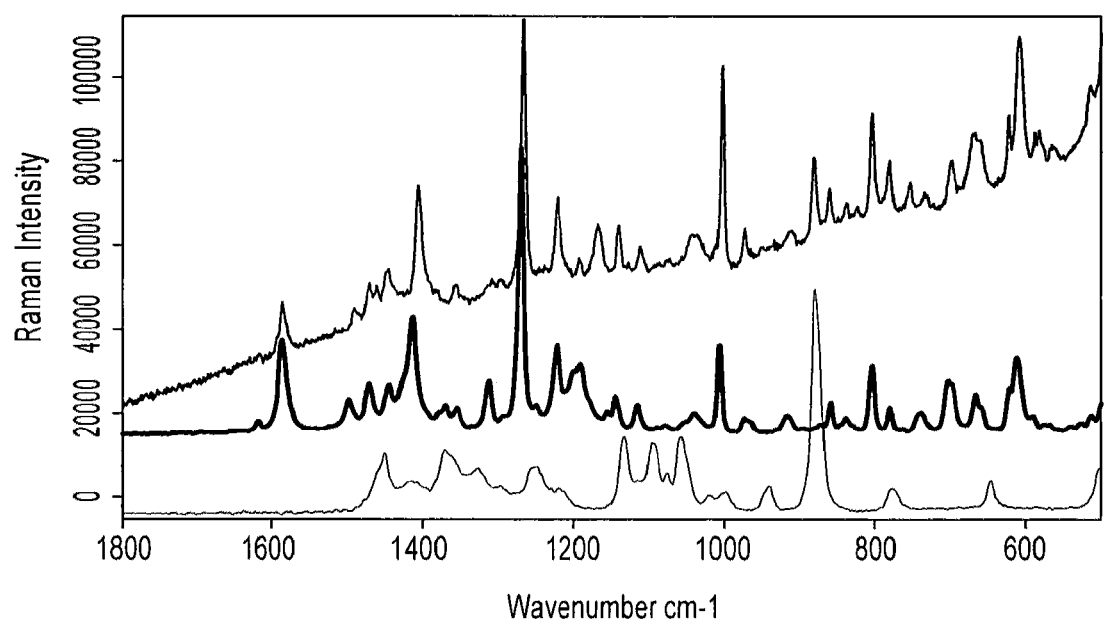
FIG. 6 is a plot of a detailed region (1800-500 cm$^{-1}$) of Raman spectra of the following (from top to bottom): a possible sorbitol co-crystal, the free drug (middle spectrum), and a co-crystal former sorbitol (bottom spectrum). The spectra have been scaled and offset in the y-direction for purposes of comparison.

The Raman spectra is shown in FIG. 6. FIG. 6 is a plot of a detailed region (1800-500 cm$^{-1}$) of a Raman spectra of the following (from top to bottom): a possible sorbitol co-crystal, the free drug (middle spectra), and a co-crystal former sorbitol (bottom spectra). The spectra have been scaled and offset in the y-direction for purposes of comparison.

Results from Evaporation Experiments

A summary of the screening results based on visual inspection and Raman spectroscopy is given in Table 3.

TABLE 3

(Screening results from SP134-X-P3 (evaporation study) based on visual inspection and Raman spectroscopy)

| Salt/Co-Crystal (Code) | Well | Solvent | Visual Inspection | Raman Spectroscopy |
|---|---|---|---|---|
| Sorbitol (SBT) | F3 | EtOH | light solid | Spectrum in F3 not useful. |
|  | F6 | EtOAc | light solid | Spectra in F6, F9 might |
|  | F9 | THF | light solid | correspond to co-crystal. |
|  | F12 | MeCN | light solid | Spectrum of FD in F12. |

Results from Suspension Equilibration Experiments

Raman Microscopy was employed with a Renishaw InVia stabilized diode laser with 785-nm excitation, an NIR-enhanced Peltier-cooled CCD camera as a detector, a long working distance 20× objective and a 2000-100 cm$^{-1}$ range.

A summary of the screening results based on visual inspection and Raman spectroscopy is given in Table 4.

TABLE 4

(Screening results from experiment SP134-X-P4 (suspension study) based on visual inspection and Raman microscopy)

| Salt/Co-Crystal | Well | Solvent | Visual Inspection | Raman Spectroscopy |
|---|---|---|---|---|
| Sorbitol (SBT) | F3 | EtOH/heptane (1:1) | light solid | Spectra obtained in wells F3, F6, and F9 might |
|  | F6 | EtOAc | light solid | correspond to co-crystal, |
|  | F9 | TBME | light solid | same as in P2. |
|  | F12 | MeCN/H$_2$O (1:1) | light solid | Spectrum in F12 is not useful. |

Scale-Up and Characterization of the Sorbitol Co-Crystal

Figure 7:
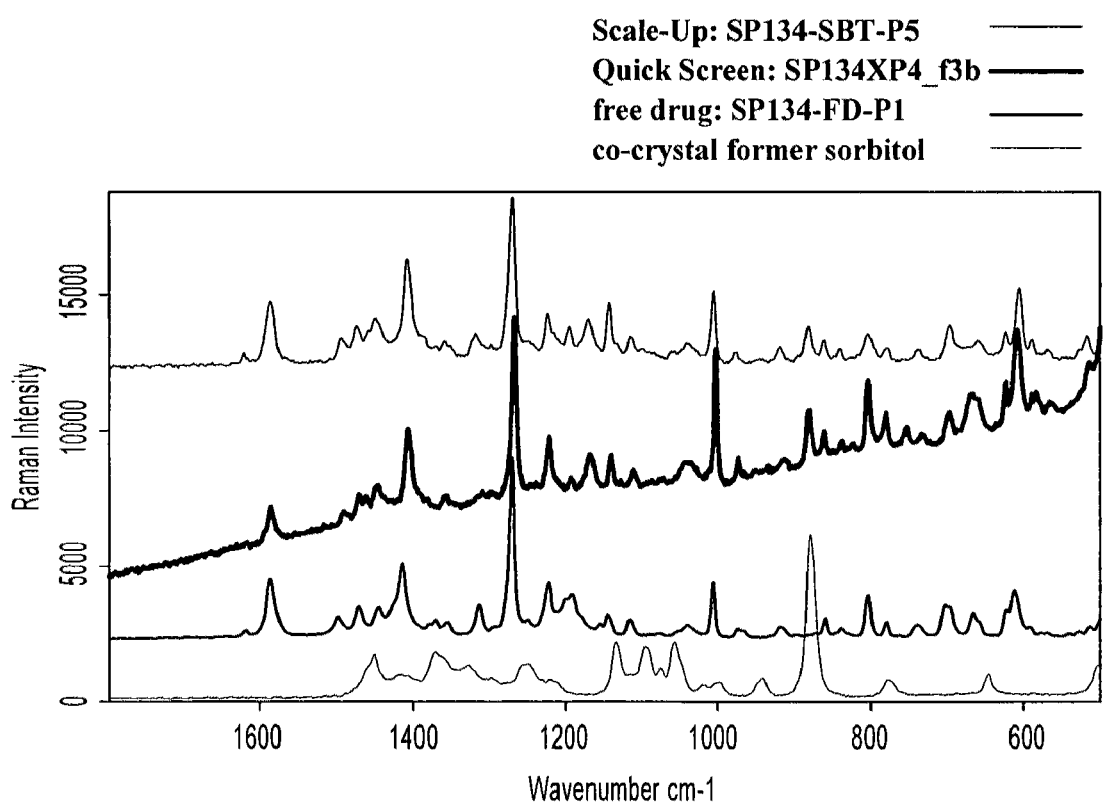
FIG. 7 is a plot of an FT-Raman spectrum (1800-500 cm-1) of the solid obtained in the scale-up experiment SP134-SBT-P5 compared to the spectra of the quick-screen lead, the free drug, and the free sorbitol co-crystal former. From top to bottom: SP134-SBT-P5, quick-screen lead SP134XP4_f3b, free drug SP134-FD-P1, free sorbitol co-crystal former.
Figure 8:
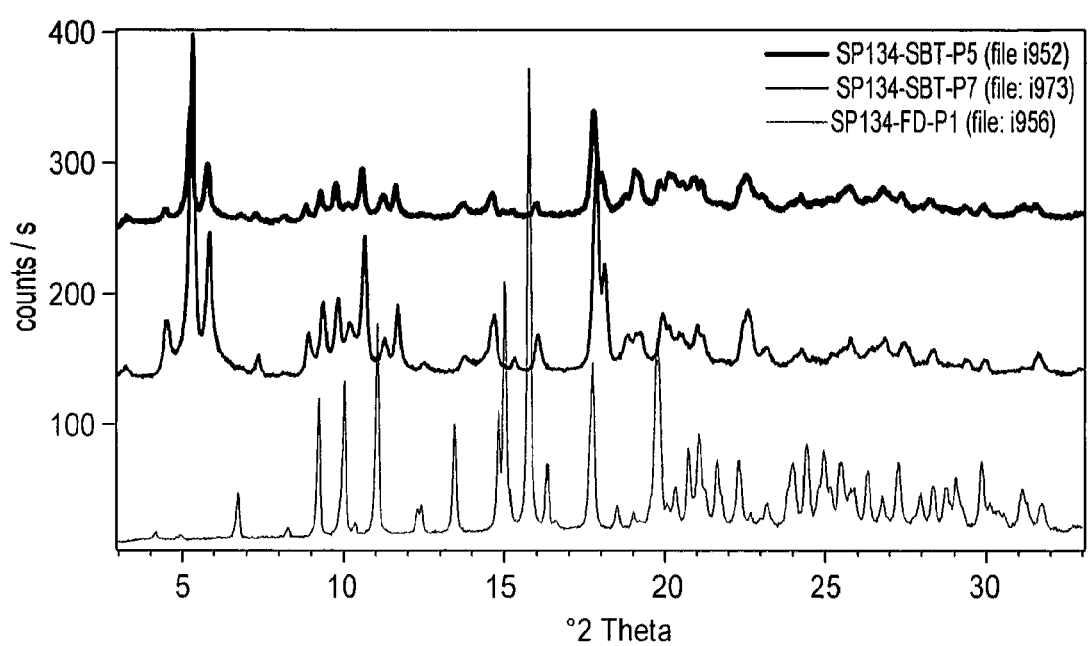
FIG. 8 is a plot of XRPD patterns of the solids obtained in the scale-up experiments SP134-SBT-P5 and SP134-SBT-P7 compared to the pattern of the free drug. From top to bottom: SP134-SBT-P5, SP134-SBT-P7, free drug SP134-FD-P1.
Figure 9:
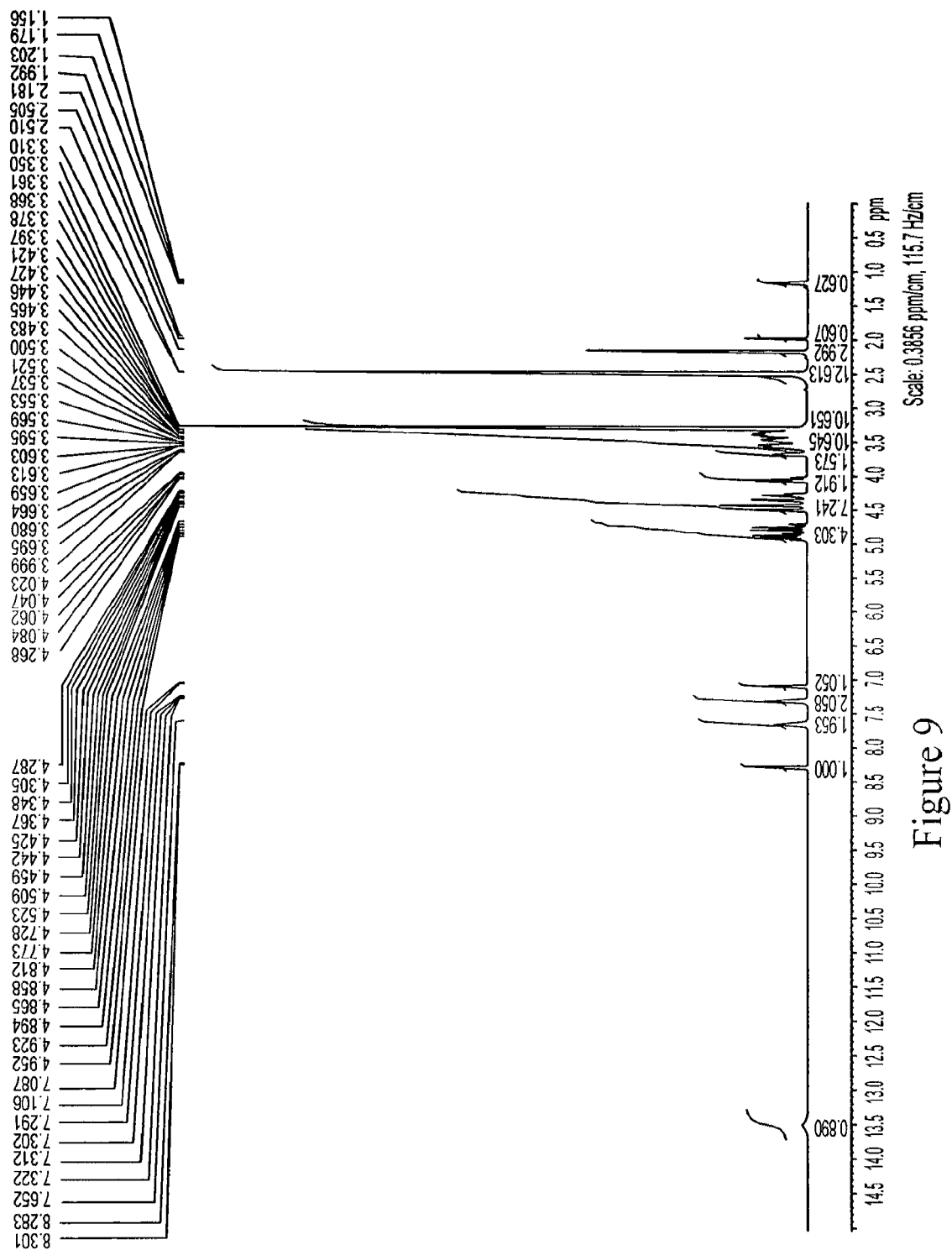
FIG. 9 is a plot of a $^1$H-NMR spectrum of the sample SP134-SBT-P5 showing a free drug to sorbitol ratio of 1:1.5 and 0.2 mole equivalent of EtOAc solvent residue.

The scale-up experiment SP134-SBT-P5 (Table 7) reproduced the quick-screen result from well P4-F6, as the comparison of the Raman spectra in FIG. 7. The spectrum showed significant shifts and differences compared to the spectrum of the free drug substance and to the free co-crystal former sorbitol. In FIG. 8, the XRPD pattern of sample SP134-SBT-P5 showed that the sample is at least partially crystalline. The pattern does not correspond to the pattern of the free drug substance or the free sorbitol co-crystal former. The $^1$H-NMR spectrum of sample SP134-SBT-P5 corresponded with a 1:1.5 ratio of free drug to sorbitol (FIG. 9). No decomposition was observed. The sample contained 0.2 mole-equiv solvent residues (EtOAc), likely due to incomplete drying.

Further experiments were carried out to reproduce this possible sorbitol co-crystal and to improve its crystallinity.

Test SP134-SBT-P6 in 1:1 EtOH/H$_2$O produced a dark brown solid (Table 5). The FT-Raman spectrum corresponds to a mixture of the free drug and the possible co-crystal. As neither purity nor crystallinity was improved, no further characterization was carried out.

Test SP134-SBT-P7 (Table 5) produced a white solid, the FT-Raman spectrum reproduced the spectrum of the quick screen lead and the scale-up experiment SP134-SBT-P5. The XRPD of SP134-SBT-P7 also corresponds to the pattern of SP134-SBT-P5. The sharper, more intense peaks indicate an improvement in crystallinity (FIG. 8). The further characterization of sample SP134-SBT-P7 is described in detail below.

Experiment SP134-SBT-P8 was a repetition of experiment SP134-SBT-P7 in order to produce more material for solubility tests with multiple determinations over time.

TABLE 5

(Scale-up experiments for the Sorbitol Co-crystal)

| Sample | Method | Characterization | Result |
|---|---|---|---|
| SP134-SBT-P5 | repeated quick screen P4-F6: equimolar suspension in EtOAc. | visual charact. FT-Raman XRPD $^1$H-NMR | white powder corresponds to quick screen partially crystalline, not FD or ccf agrees to 1:1.5 ratio FD/ccf |
| SP134-SBT-P6 | combined clear solutions (FD in EtOH, ccf in H$_2$O), 1:1 ratio FD/ccf. | visual charact. FT-Raman | dark brown solid corresponds to mixture of free drug and SP134-SBT-P5 |
| SP134-SBT-P7 | combined clear solutions (FD in EtOAc, ccf in DMSO), 1:1.5 ratio FD/ccf. | visual charact. FT-Raman XRPD | white powder corresponds to SP134-SBT-P5 corresponds to SP134-SBT-P5, higher crystallinity and further characterization below. |
| SP134-SBT-P8 | same procedure as for SP134-SBT-P7 | FT-Raman | white powder corresponds to SP134-SBT-P7 |

FIG. 7 is a plot of a FT-Raman spectrum (1800-500 cm-1) of the solid obtained in the scale-up experiment SP134-SBT-P5 compared to the spectra of the quick-screen lead, the free drug and the free sorbitol co-crystal former. The spectra have been scaled and offset in the y-direction for purposes of comparison.

FIG. 8 is a plot of XRPD patterns of the solids obtained in the scale-up experiments SP134-SBT-P5 and SP134-SBT-P7 compared to the pattern of the free drug. The patterns have been offset in the y-direction for purposes of comparison.

FIG. 9 is a plot of 1H-NMR spectrum of the sample SP134-SBT-P5 showing a free drug to sorbitol ratio of 1:1.5 and 0.2 mole equivalent of EtOAc solvent residue.

Characterization of the Sorbitol Co-Crystal

The sorbitol co-crystal (sample SP134-SBT-P7) was further characterized by $^1$H-NMR, TG-FTIR, DSC, DVS, elemental composition analysis and aqueous solubility. The results are summarized in Table 6.

TABLE 6

(Summary of characterization results of the sorbitol co-crystal (sample: SP134-SBT-P7)

Figure 10:
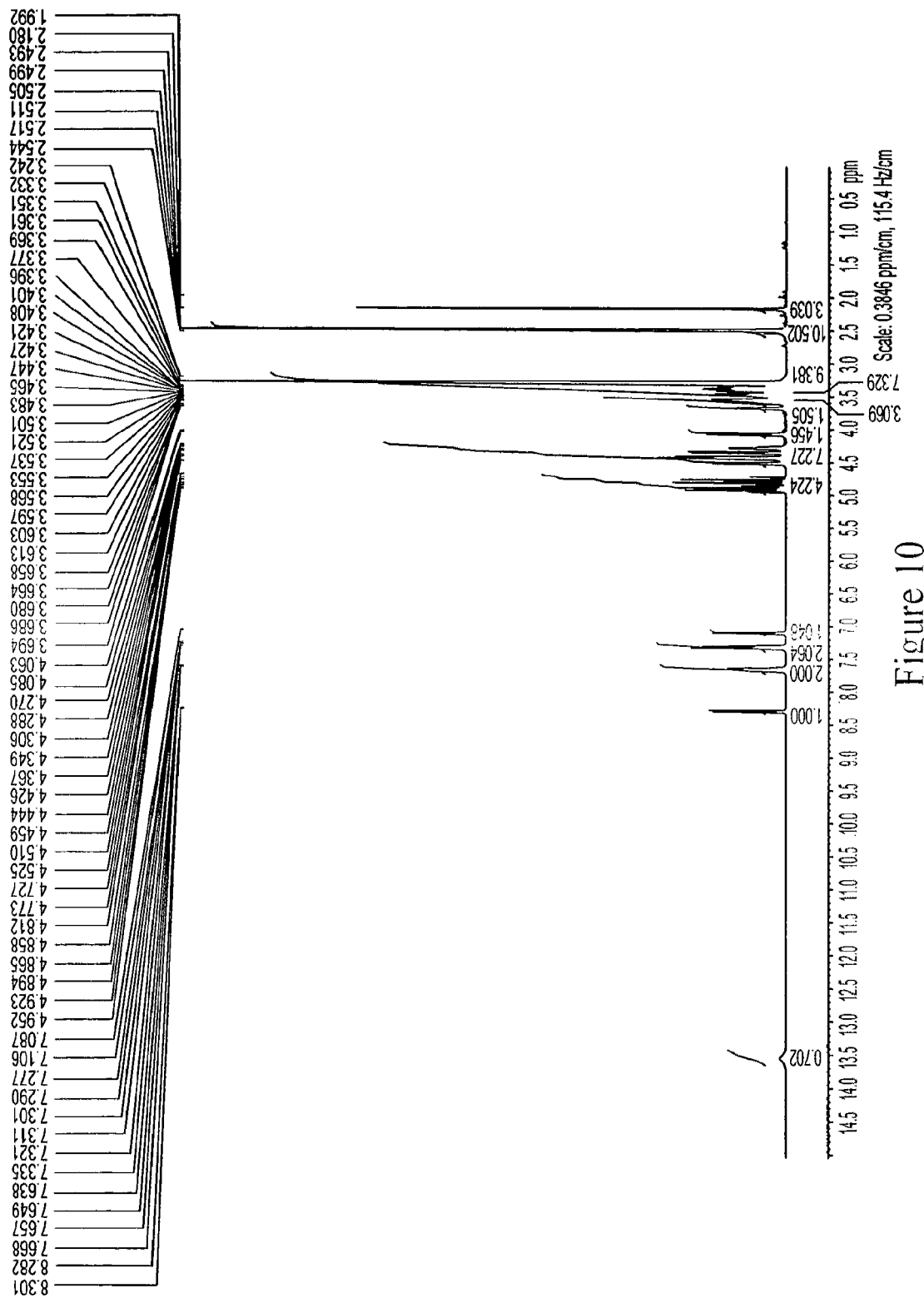
FIG. 10 is a plot of a $^1$H-NMR spectrum of sample SP134-SBT-P7 (1:1.5 dexlansoprazole-sorbitol co-crystal).
Figure 11:
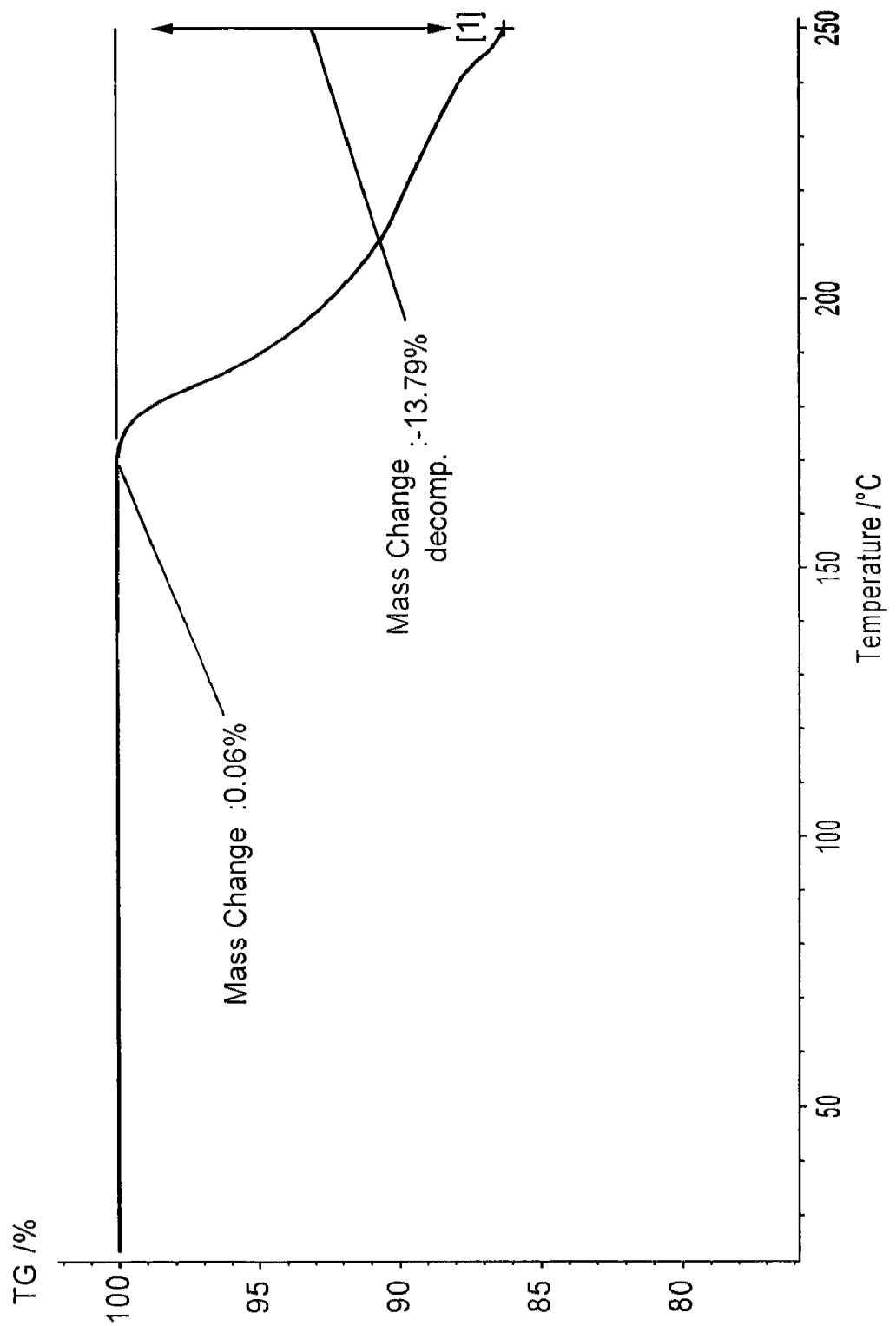
FIG. 11 is a plot of a TG-FTIR of sample SP134-SBT-P7 (1:1.5 dexlansoprazole-sorbitol co-crystal).
Figure 12:
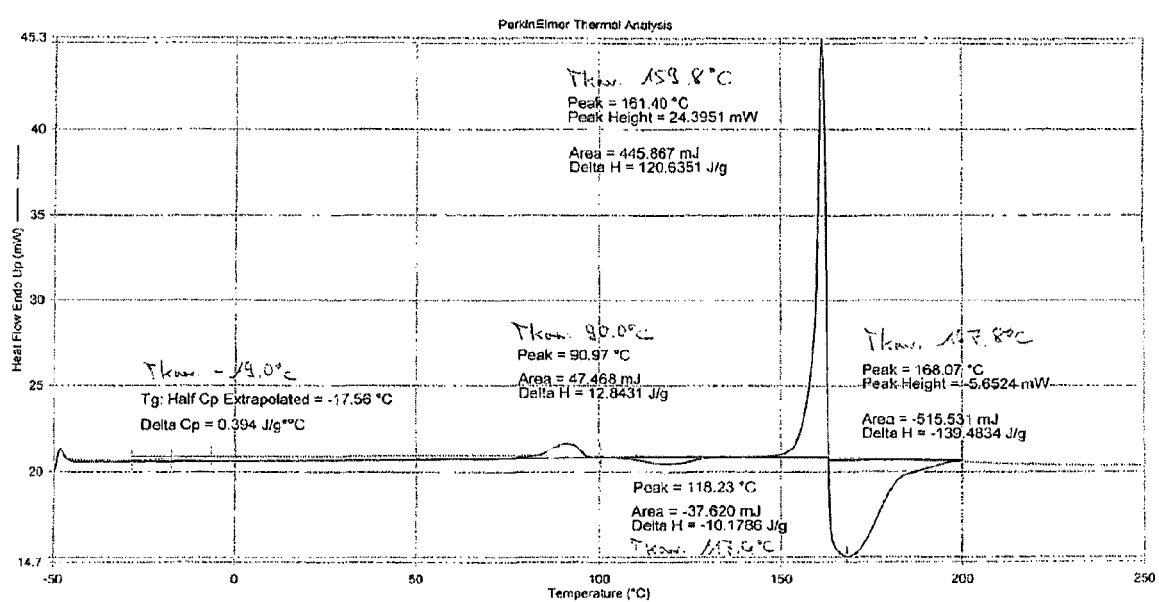
FIG. 12 is a plot of a differential scanning calorimetry (DSC) of sample SP134-SBT-P7 (1:1.5 dexlansoprazole-sorbitol co-crystal).
Figure 13:
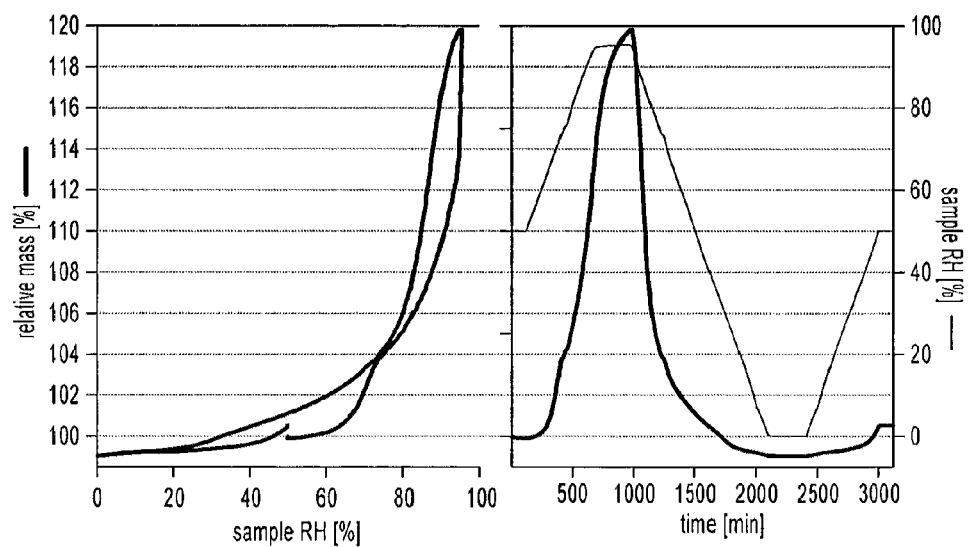
FIG. 13 is a plot of a dynamic vapor sorption (DVS) of sample SP134-SBT-P7 (1:1.5 dexlansoprazole-sorbitol co-crystal). Curve in left panel and bottom curve in right panel: relative mass [%]; top curve in right panel: sample RH [%].

| Method | Result | |
|---|---|---|
| FT-Raman | corresponds to quick screen lead and SP134-SBT-P5 | |
| XRPD | corresponds to SP134-SBT-P5, improved crystallinity | FIG. 8 |
| $^1$H-NMR | agrees with 1:1.5 ratio of FD to ccf, no significant impurities found | FIG. 10 |
| TG-FTIR | no loss 25-170° C., >170° C. decomposition | FIG. 11 |
| DSC | small endo- and exothermic events (90° C., ΔH = +12.8 J/g and 117° C., ΔH = −10.2 J/g); sharp endothermic peak (max at 160° C., ΔH = +120.6 J/g); immediately followed by exothermic decomposition (167° C., ΔH = −139.5 J/g) | FIG. 12 |
| DVS | reversible weight gain with step at 4 wt.-% (~70-75% r.h.), gain of ~7 wt.-% at 85% r.h.; i.e. hygroscopic; gain and loss reversible. | FIG. 13 |

TABLE 6-continued (Summary of characterization results of the sorbitol co-crystal (sample: SP134-SBT-P7)

| Method | Result | |
|---|---|---|
| Elemental Analysis | consistent with a co-crystal with a 1:1.5 ratio of FD to ccf | Table 7 |
| Aq. Solubility | solid form not stable in $H_2O$ for 24 h, disintegrates into the FD and sorbitol. | Table 8 |

The $^1$H-NMR spectrum of sample SP134-SBT-P7 confirmed a 1:1.5 ratio of free drug to sorbitol co-crystal former (FIG. 10). No decomposition or solvent residues were observed.

The TG-FTIR of sample SP134-SBT-P7 showed no mass loss from 25 to 170° C., i.e. no solvent or water content. Decomposition started at ~170° C. (FIG. 11).

The DSC of sample SP134-SBT-P7 showed a small endotherm at 90° C. ($\Delta H=12.8$ J/g) followed by an exotherm at 117° C. ($\Delta H=-10.2$ J/g). A sharp endothermic peak, possibly attributable to melting, can be observed at 160° C. ($\Delta H=120.6$ J/g), followed directly by decomposition (exotherm) (FIG. 12). As the sample decomposed at least partially, the glass transition temperature observed in the second scan at $T_g=-19°$ C. was null.

In the DVS of sample SP134-SBT-P7 (FIG. 13), the relative humidity (r.h.) was cycled from 50% r.h. to 95% r.h. to 0% r.h. and back to 50% r.h. The sample showed a reversible weight gain of 20 wt.-% as the relative humidity was raised to 95% with a step at ~4 wt.-% (70-75% r.h.) indicating the existence of a monohydrate (theoretical water contents: 4.5 wt.-%). It did not seem to have reached equilibrium at 95% r.h. Upon lowering the relative humidity to 0%, the water was readily desorbed (again with a small step at ~4 wt.-%), at 50% r.h. the sample weight is increased by ~1 wt. % relative to the starting weight. Upon lowering the relative humidity further to 0% a weight loss of <1 wt.-% (relative to the starting weight) occurred. Thus, the sample was hygroscopic. The post-DVS FT-Raman spectrum showed no significant changes compared to the reference spectrum.

The elemental composition analysis agreed with a 1:1.5 ratio of free drug to sorbitol co-crystal former (Table 7). No solvent or other contributions were measured.

TABLE 7

(Elemental analysis of SP134-SBT-P7)

| | % C | % H | % N | % O | % S | % F | Σ |
|---|---|---|---|---|---|---|---|
| SP134-SBT-P7 (experimental) | 45.97 | 5.51 | 6.62 | 27.22 | 5.16 | 9.01 | 99.47 |
| SP134-SBT-P7 (experimental, normalized to 100%) | 46.21 | 5.54 | 6.65 | 27.36 | 5.18 | 9.06 | 100.00 |
| $C_{16}H_{14}N_3O_2SF_3$ $1.5xC_6H_{14}O_6$ (theoretical 1:1.5 co-crystal) | 46.73 | 5.49 | 6.54 | 27.39 | 4.99 | 8.87 | 100.01 |
| difference (expt. (norm.) − theo.) | 0.52* | 0.05 | 0.11 | −0.03 | 0.19 | 0.19 | −0.01 |

*Difference exceeded the measurement error of ±0.3%.

The solubility of SP134-SBT-P7 in water was measured after 24 hours of equilibration at 22° C. as 0.18 mg/mL. The pH of the corresponding saturated solution was 6.1. However, as the Raman spectrum of the solid residue agreed with that of the free drug rather than that of the sorbitol co-crystal, the measured solubility did not correspond to the sorbitol co-crystal, but to the free drug. Additional signals were observed in the sample after 24 hours equilibration in $H_2O$ indicate decomposition of the sample. This may be due to chemical instability of dexlansoprazole in the solution environment.

A further experiment to evaluate the kinetic solubility was carried out. The solubility of the co-crystal was monitored at time various time intervals as shown in Table 8. The maximum was reached already after 15 minutes and that the concentration in the solution remained constant for the duration of the experiment.

TABLE 8

(Result from kinetic solubility experiment in water given in mg dexlansoprazole per ml)

| Sample/Solubility | 15 min | 30 min | 1 hour | 2 hour | 4 hrs. | 8 hrs. |
|---|---|---|---|---|---|---|
| SP122-SBT-P8 | 0.25 | 0.26 | 0.26 | 0.24 | 0.27 | 0.27 |

FIG. 10 is a plot of a 1H-NMR spectrum of sample SP134-SBT-P7 showing a free drug to ratio of 1:1.5 and no decomposition or solvent residues. FIG. 11 is a plot of a TG-FTIR of the sorbitol co-crystal SP134-SBT-P7. The sample contained no solvent/water. Decomposition began at ~160° C. FIG. 12 is a plot of a DSC of sample SP134-SBT-P7. FIG. 13 is a plot of a DVS of sample SP134-SBT-P7.

Peak lists for the FT-Raman spectrum and the XRPD pattern of the sorbitol co-crystal (sample SP134-SBT-P7) were compiled and are shown below in FIGS. 14 and 15 and Tables 9 and 10.

TABLE 9

(Peak list (range: 3400-100 cm-l, sensitivity: 2.5%) of the FT-Raman spectrum of SP134-SBT-P7)

| wavenumber | abs. intensity | rel. intensity | width | found when limit < |
|---|---|---|---|---|
| 3093.01 | 0.03 | 0.01 | 7.75 | 5.74 |
| 3072.76 | 0.04 | 0.03 | 14.32 | 17.01 |
| 2964.51 | 0.05 | 0.01 | 5.08 | 3.89 |
| 2951.87 | 0.06 | 0.06 | 7.42 | 32.22 |
| 2931.70 | 0.05 | 0.01 | 14.22 | 4.17 |
| 2886.17 | 0.04 | 0.01 | 24.20 | 4.85 |
| 2709.09** | 0.01 | 0.00 | 7.64 | 2.50 |
| 1618.93 | 0.02 | 0.01 | 4.69 | 2.59 |
| 1585.55 | 0.07 | 0.06 | 12.66 | 34.17 |
| 1490.45 | 0.03 | 0.01 | 8.87 | 5.40 |
| 1471.59 | 0.05 | 0.01 | 7.07 | 6.45 |
| 1447.39 | 0.06 | 0.03 | 10.15 | 14.63 |
| 1406.21 | 0.11 | 0.10 | 10.69 | 56.34 |
| 1358.56 | 0.03 | 0.01 | 10.62 | 5.93 |
| 1312.28 | 0.03 | 0.01 | 22.55 | 4.47 |
| 1268.45 | 0.17 | 0.17 | 9.09 | 100.37 |
| 1222.40 | 0.06 | 0.04 | 8.87 | 22.83 |
| 1195.04 | 0.04 | 0.01 | 7.19 | 7.22 |
| 1168.80 | 0.05 | 0.03 | 11.27 | 16.57 |
| 1142.07 | 0.05 | 0.03 | 7.50 | 18.21 |
| 1112.00 | 0.03 | 0.01 | 8.54 | 6.79 |
| 1039.64 | 0.03 | 0.01 | 18.54 | 7.30 |
| 1003.53 | 0.08 | 0.07 | 6.63 | 39.89 |
| 974.37 | 0.02 | 0.01 | 9.51 | 5.64 |
| 917.03 | 0.02 | 0.01 | 13.26 | 5.49 |
| 881.19 | 0.05 | 0.04 | 8.26 | 24.02 |
| 861.23 | 0.03 | 0.01 | 6.42 | 4.93 |
| 839.12 | 0.02 | 0.01 | 6.93 | 5.70 |
| 803.70 | 0.05 | 0.04 | 7.73 | 20.26 |
| 780.40 | 0.03 | 0.01 | 6.65 | 6.77 |
| 734.89 | 0.02 | 0.01 | 11.99 | 3.23 |
| 697.76 | 0.04 | 0.03 | 10.51 | 15.98 |
| 665.02 | 0.04 | 0.02 | 19.32 | 8.89 |
| 623.07 | 0.04 | 0.01 | 4.80 | 4.35 |

TABLE 9-continued (Peak list (range: 3400-100 cm-1, sensitivity: 2.5%)
of the FT-Raman spectrum of SP134-SBT-P7)

| wavenumber | abs. intensity | rel. intensity | width | found when limit < |
|---|---|---|---|---|
| 607.24 | 0.07 | 0.06 | 11.87 | 33.06 |
| 588.09 | 0.03 | 0.01 | 5.71 | 3.07 |
| 515.40 | 0.03 | 0.01 | 9.19 | 6.13 |
| 498.14 | 0.04 | 0.02 | 6.18 | 13.90 |
| 404.88 | 0.02 | 0.01 | 17.34 | 3.54 |
| 353.31 | 0.02 | 0.01 | 13.24 | 2.73 |
| 303.28 | 0.03 | 0.02 | 10.52 | 8.49 |
| 235.05 | 0.03 | 0.01 | 11.08 | 7.51 |
| 186.75 | 0.07 | 0.03 | 14.35 | 17.03 |
| 121.87 | 0.14 | 0.02 | 8.44 | 9.05 |

TABLE 10

(Peak list (range: 2.5-35° 2Theta)
of the XRPD pattern of SP134-SBT-P7)

| Angle [2-Theta °] | d value [Å] | Intensity [Cps]* | Intensity [%] |
|---|---|---|---|
| 3.23 | 27.4 | w | 8 |
| 4.51 | 19.6 | m | 21 |
| 5.30 | 16.7 | vs | 100 |
| 5.85 | 15.1 | s | 46 |
| 7.33 | 12.1 | w | 13 |
| 8.91 | 9.9 | m | 19 |
| 9.37 | 9.4 | m | 28 |
| 9.83 | 9.0 | m | 29 |
| 10.20 | 8.7 | m | 22 |
| 10.64 | 8.3 | s | 47 |
| 11.29 | 7.8 | m | 18 |
| 11.67 | 7.6 | m | 28 |
| 12.49 | 7.1 | w | 10 |
| 13.77 | 6.4 | w | 13 |
| 14.66 | 6.0 | m | 25 |
| 15.29 | 5.79 | w | 12 |
| 16.02 | 5.53 | m | 19 |
| 17.83 | 4.97 | s | 69 |
| 18.09 | 4.90 | s | 41 |
| 18.79 | 4.72 | m | 19 |
| 19.20 | 4.62 | m | 19 |
| 19.93 | 4.45 | m | 25 |
| 20.13 | 4.41 | m | 22 |
| 20.51 | 4.33 | m | 19 |
| 20.98 | 4.23 | m | 22 |
| 21.18 | 4.19 | m | 19 |
| 22.57 | 3.94 | m | 27 |
| 23.15 | 3.84 | m | 16 |
| 24.25 | 3.67 | m | 15 |
| 25.19 | 3.53 | w | 14 |
| 25.78 | 3.45 | m | 19 |
| 26.41 | 3.37 | w | 14 |
| 26.82 | 3.32 | m | 19 |
| 27.43 | 3.25 | m | 17 |
| 28.31 | 3.15 | w | 15 |
| 29.36 | 3.04 | w | 11 |
| 29.94 | 2.98 | w | 11 |
| 31.60 | 2.83 | w | 14 |
| 34.21 | 2.62 | w | 10 |

Figure 14:
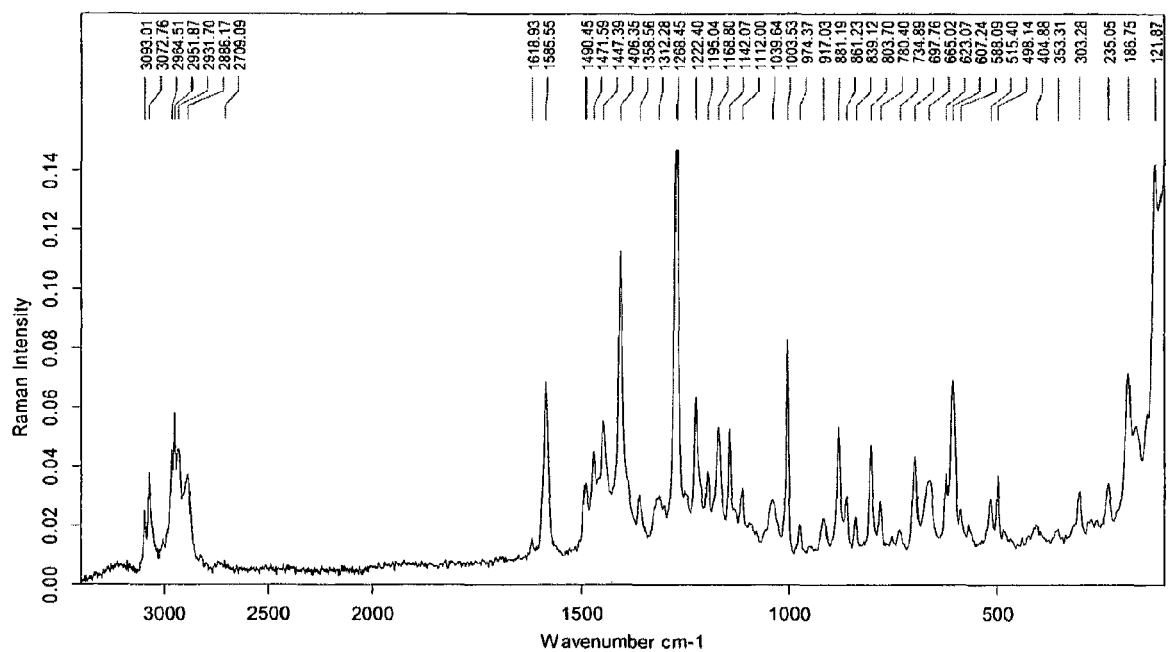
FIG. 14 is a plot of an FT-Raman of sample SP134-SBT-P7 (1:1.5 dexlansoprazole-sorbitol co-crystal).
Figure 15:
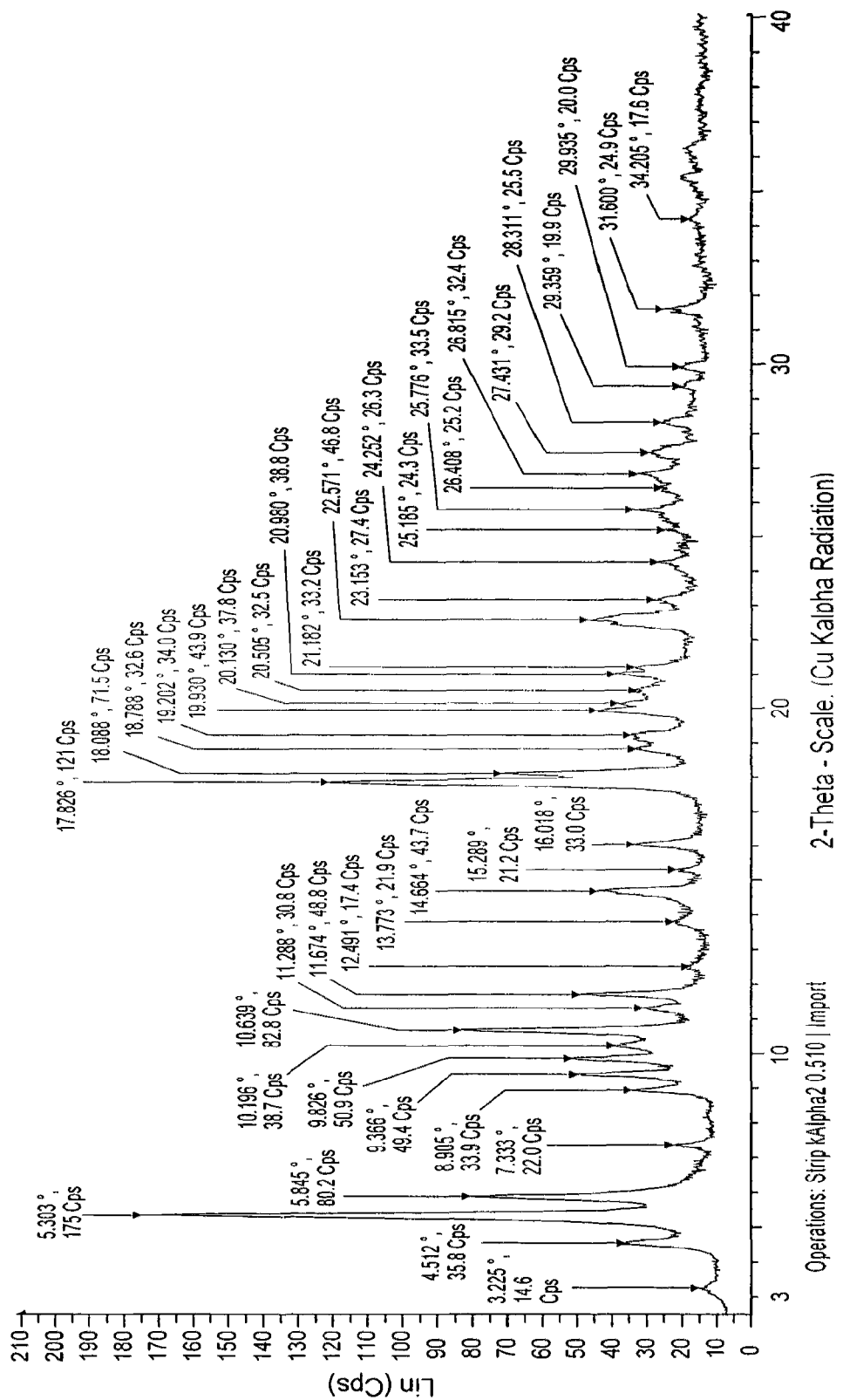
FIG. 15 is a plot of an XRPD pattern of sample SP134-SBT-P7 (1:1.5 dexlansoprazole-sorbitol co-crystal) with labeled peaks.

FIG. 14 is a plot of a FT-Raman of the sorbitol co-crystal of the sample SP134-SBT-P7 including peak picking. FIG. 15 is a plot of a XRPD of the sorbitol co-crystal of sample SP134-SBT-P7 with labeled peaks.

Example 2

Summary of Results

Based on the outcome of the co-crystal screening for dexlansoprazole in Example 1, a crystallization study was performed to develop a controlled, seeded cooling crystallization process to produce the dexlansoprazole-sorbitol co-crystal reliably and reproducibly. Amorphous dexlansoprazole (batch PL-36-015) was used as starting material.

In contrast to the co-crystal screening for dexlansoprazole in Example 1, where a 1:1.5 dexlansoprazole-sorbitol co-crystal was obtained, all crystallization samples in Example 2 show a 1:1 stoichiometry.

A first series of experiments was carried out on a 500 mg scale in order to find a suitable solvent system and crystallization conditions. Several solvent systems were evaluated. DMSO/EtOH was chosen based on the relatively high solubility of sorbitol at higher temperatures (40-60° C.). The desired co-crystal also showed a relatively high solubility at 40° C., but was less soluble than sorbitol and dexlansoprazole.

Crystallization experiments on a 6-10 g scale were performed in a Mettler Toledo Multimax system equipped with an FBRM lasentec probe (allows for in-situ determination of particle chord lengths). The process was optimized with respect to the starting concentration and seeding. In order to obtain information about the robustness, an increased cooling rate was tested. The obtained solids were analyzed by FT-Raman, PXRD, TG-FTIR and optical microscopy. Two of the samples were also analyzed by DSC, HPLC for chemical purity, DVS and Karl Fischer.

The best crystallization experiments performed with respect to product yield and crystallinity were SP134-SBT-P26 and SP134-SBT-P27. Both experiments were carried out with the same initial co-crystal concentration (68-69 mg/mL) and the same amount of seed crystals (2%). SP134-SBT-P26 was performed with a cooling rate of 0.1 K/min. In order to obtain information about the robustness, SP134-SBT-P27 was cooled with a rate of 0.2 K/min. In both experiments, the 1:1 dexlansoprazole-sorbitol co-crystal was obtained with a yield of 83% and 78%, respectively.

Characterization of Starting Material

Figure 16A:
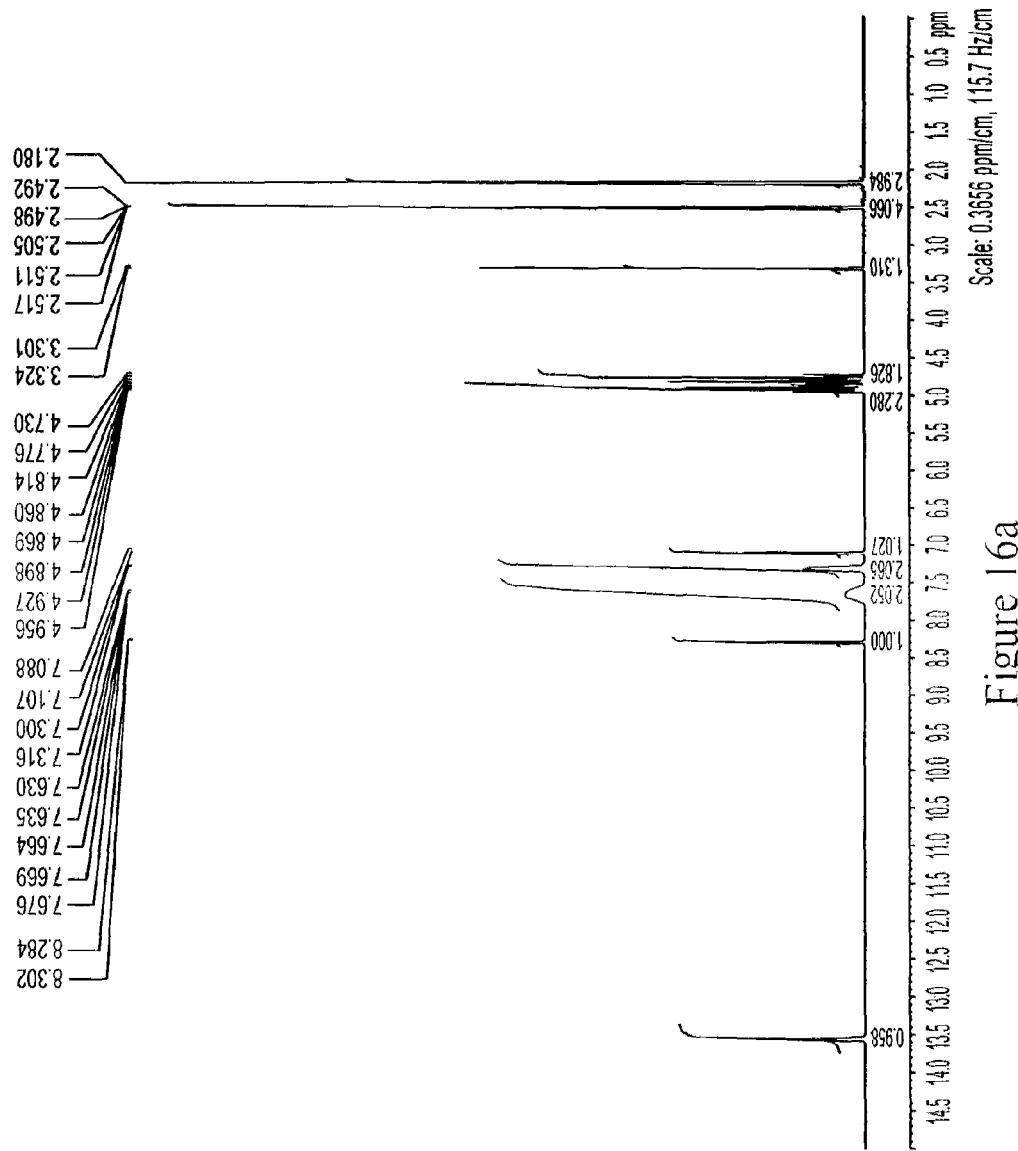
FIG. 16a is $^1$H-NMR spectrum of amorphous dexlansoprazole in DMSO-d6, batch PL-36-015 (SP134-FD-P3).
Figure 16B:
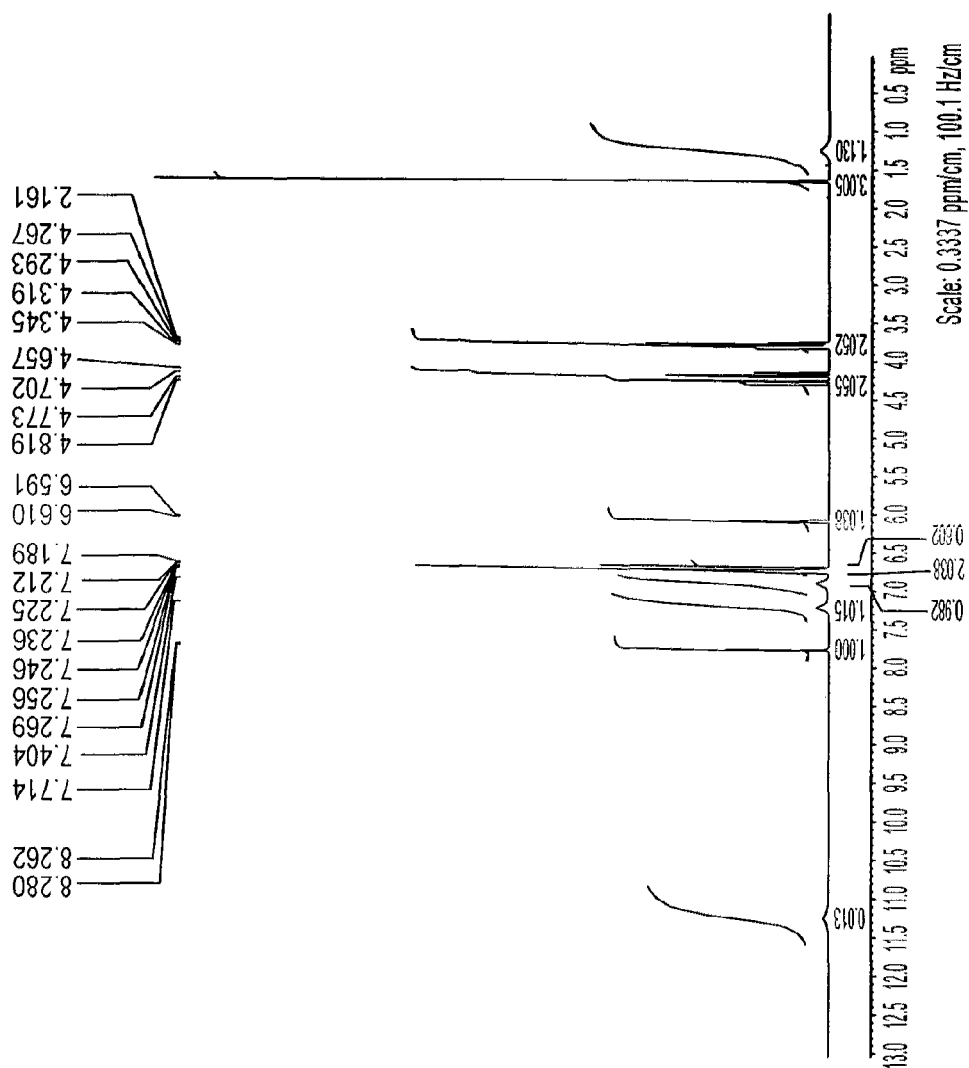
FIG. 16b is $^1$H-NMR spectrum of amorphous dexlansoprazole in CDCl$_3$, batch PL-36-015 (SP134-FD-P3).

A $^1$H-NMR was recorded of the amorphous dexlansoprazole sample, batch PL-36-015 (SP134-FD-P3) in DMSO-d6 (FIG. 16a). Dexlansoprazole, batch PL-36-015 (SP134-FD-P3) was also analyzed in $CDCl_3$ (FIG. 16b).

Figure 17:
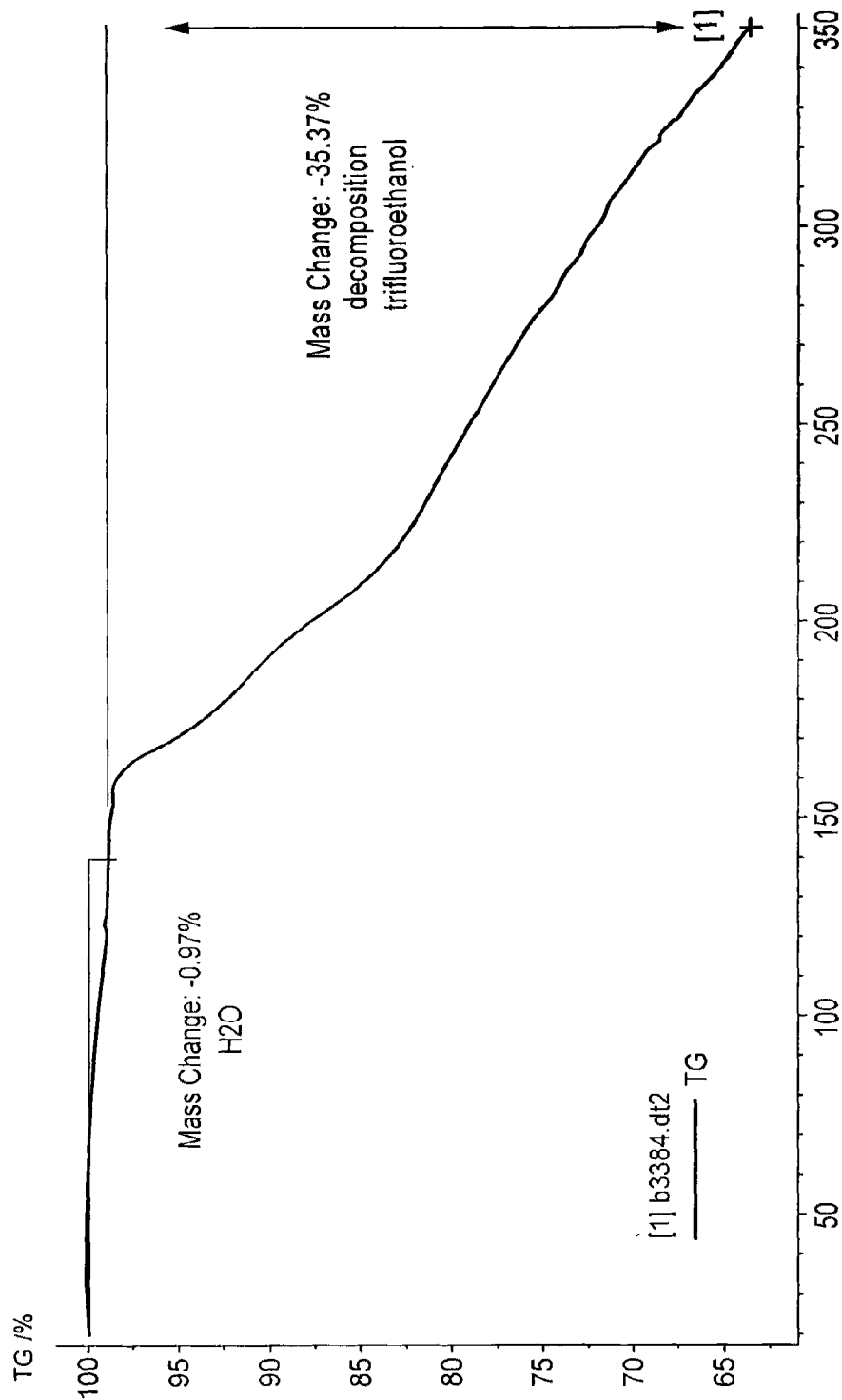
FIG. 17 is TG-FTIR of amorphous dexlansoprazole, batch PL-36-015 (SP134-FD-P3).

Amorphous dexlansoprazole, batch PL-36-015 (SP134-FD-P3) was analyzed by TG-FTIR in a temperature range from 25° C. to 350° C. and with a heating rate of 10° C./min. The TG-FTIR (FIG. 17) shows a mass loss of 1 wt.-% from room temperature to 140° C. This weight loss is attributable to water. Decomposition starts at temperatures >150° C.

The approximate solubilities of the sorbitol co-crystal former were estimated at 60° C. and of the 1:1 dexlansoprazole-sorbitol co-crystal at 40° C. and 10° C. Dexlansoprazole is sufficiently soluble in many typical organic solvents. The approximate solubility was tested in different solvent mixtures by manual dilution combined with visual observation (see Table 11 and Table 12). The solubility values presented are intended to be regarded as rough estimates and are to be used solely for the design of crystallization experiments. All solvent mixtures are listed as ratios by volume (v/v).

TABLE 11

Approximate solubility of the sorbitol co-crystal former at 60° C.

| Solvent | 1:1 DMSO/ EtOH | 1:3 DMSO/ EtOH | 1:5 DMSO/ EtOH | 1:1 EtoAc/ EtOH | 1:2 EtoAc/ EtOH | 1:3 EtoAc/ EtOH | 1:5 EtoAc/ EtOH |
|---|---|---|---|---|---|---|---|
| Sorbitol Solubility [mg/ml] | >102 | 54-108 | 39-59 | 3 | 6 | 10 | 11 |

TABLE 12

Approximate solubility of the 1:1 dexlansoprazole-sorbitol co-crystal at 40° C. and 10° C.

| Solvent Mixture | 40° C. | 10° C. |
|---|---|---|
| 1:5 DMSO/EtOH | 17-23 mg/mL | 9.3-9.8 mg/mL |
| 1:4 DMSO/EtOH | >37 mg/mL | 11.5-12.5 mg/mL |
| 1:3 DMSO/EtOH | 50-63 mg/mL | 14-16 mg/mL |

Crystallization Experiments

A first series of experiments was carried out on a 500 mg scale in order to find a suitable solvent system and crystallization conditions (SP134-SBT-P16 to -P21). Crystallization experiments on the 6-10 g scale were performed in a Mettler Toledo Multimax system equipped with an FBRM lasentec probe (allows for in-situ determination of particle chord lengths) (SP134-SBT-P22 to -P27). The process was optimized with respect to the starting concentration and seeding (SP134-SBT-P22 to -P26). In order to get some information about the robustness, an increased cooling rate was tested (SP134-SBT-P27). The obtained solids were analyzed by FT-Raman, PXRD, TG-FTIR and optical microscopy. Two of the samples were also analyzed by DSC, chemical purity, DVS and Karl Fischer (SP134-SBT-P26 and -P27).

Solvent System

Ethanol/DMSO, ethyl acetate/DMSO and ethanol/ethyl acetate were evaluated. DMSO/EtOH (1:5; v:v) was chosen based on the relatively high solubility of sorbitol at higher temperatures (40-60° C.). The desired co-crystal was at 40° C. less soluble than sorbitol and dexlansoprazole.

500 mg-Scale Experiments (SP134-SBT-P16-SP134-SBT-P21)

Non-seeded cooling crystallization experiments on a 500 mg-scale were performed with different solvent systems and different initial concentrations. The aim of the crystallization experiments was to find a robust process in order to obtain the 1:1 dexlansoprazole-sorbitol co-crystal in an ICH class 3 solvent or solvent mixture with good volume efficiency and with a high yield.

All experiments were conducted according to the following general scheme: The sorbitol was dissolved in the solvent mixture at the corresponding dissolution temperature (room temperature up to 60° C.); care was taken that all material dissolved and a clear solution was obtained; the clear solution was cooled or heated to the crystallization start temperature of 40° C. Dexlansoprazole was dissolved in the solvent mixture at room temperature, care was taken that all material dissolved and a clear solution was obtained. The dexlansoprazole solution (FD-solution) was slowly added to the sorbitol solution (CCF-solution) at 40° C. The solution/suspension was cooled with a cooling rate of 0.1 K/min to 10° C. and stirred at 10° C. for about 30 min to several hours (e.g., from about 30 min to about 25 hours); the solid was recovered by vacuum filtration and examined by $^1$H-NMR, FT-Raman spectroscopy, PXRD, light microscopy and TG-FTIR. Additionally, four samples were analyzed by DSC and HPLC (purity analysis). For the experiments SP134-SBT-P16 to -P19 dried solvents were used. For SP134-SBT-P20 and -P21 solvents with a technical quality were used.

The DMSO/EtOH (1:5) solvent system was found to be most suitable. In all experiments a 1:1 dexlansoprazole-sorbitol co-crystal was found.

The samples contained water in a range of 0.2-1.6%, even though dried solvents (P16-P19) were used. SP134-SBT-P16 shows melting at a temperature of 161° C., which passes directly into the decomposition. Due to the higher water content of SP134-SBT-P17 and SP134-SBT-P19, the co-crystal forms most likely a eutectic with water, which melts at temperatures of about −7 to 0° C.

The HPLC purity was estimated, using a general, unoptimized method. All analyzed samples show a chemical purity of about 96% (main peak with retention time of 8.8 minutes and one additional peak at 9.3 minutes). The identity of this impurity peak is unknown. It is possible that the material decomposed due to the acidic medium on column.

6-10 g Scale Experiments (SP134-SBT-P22-SP134-SBT-P27)

At first, non-seeded cooling crystallization experiments (SP134-SBT-P22 and -P23) and then seeded cooling crystallization experiments (SP134-SBT-P24 to -P27) with amorphous dexlansoprazole as starting material on a 6-10 g scale were performed in a Mettler-Toledo MultiMax System equipped with temperature controller and sensors. All experiments were monitored using a Lasentec FBRM probe for particle size analysis. For all experiments the reactor content temperature, $T_r$, was used as the controlled variable for the temperature programs. The crystallization process was developed with respect to the following parameters: the solvent system; the initial concentration; the seeding temperature; the amount of seeding crystals; the cooling speed.

The experiments were conducted according to the following general scheme: The sorbitol was suspended in the solvent mixture at room temperature and heated to 40° C.; dexlansoprazole was also dissolved in the solvent mixture at room temperature, filtrated and slowly added to the sorbitol-solution at 40° C.; care was taken that all material was dissolved and a clear solution was obtained; the seeding crystals were added as a suspension; care was taken that not all seeding crystals dissolved and a cloudy solution/suspension was obtained; the cloudy solution/suspension was cooled to 10° C. or 2° C. and stirred at this end temperature; the solid was recovered by vacuum filtration and examined by FT-Raman spectroscopy, PXRD, light microscopy and TG-FTIR. Additionally 2-4 samples were analyzed by $^1$H-NMR; DSC, HPLC (purity analysis), DVS and Karl Fischer water content.

Experiment SP134-SBT-P22

In a first crystallization experiment an initial co-crystal concentration of 137 mg/mL was used. Sorbitol was suspended in EtOH/DMSO (5:1) at room temperature and heated to 60° C. Care was taken that all material was dissolved and a clear solution was obtained; the clear solution was cooled to the crystallization start temperature of 40° C. Dexlansoprazole was dissolved in EtOH/DMSO (5:1) at r.t. and slowly added at 40° C. to the sorbitol-solution. Selected data recorded in-situ with the FBRM probe show that during the addition the solution became turbid and afterwards the number of particles increased rapidly. Compared to the values of the approximate solubility, the solution was highly oversaturated (approximate solubility of the co-crystal at 40° C.: 17-23 mg/mL). The suspension was heated up to 45° C. and additional solvent mixture was added in order to dissolve the precipitate. Due to the limited volume of the reactor it was not possible to dissolve the precipitation. The suspension was cooled down with a cooling rate of 0.1 K/min to 10° C. and stirred at 10° C. for about 10 h.

Figure 18:
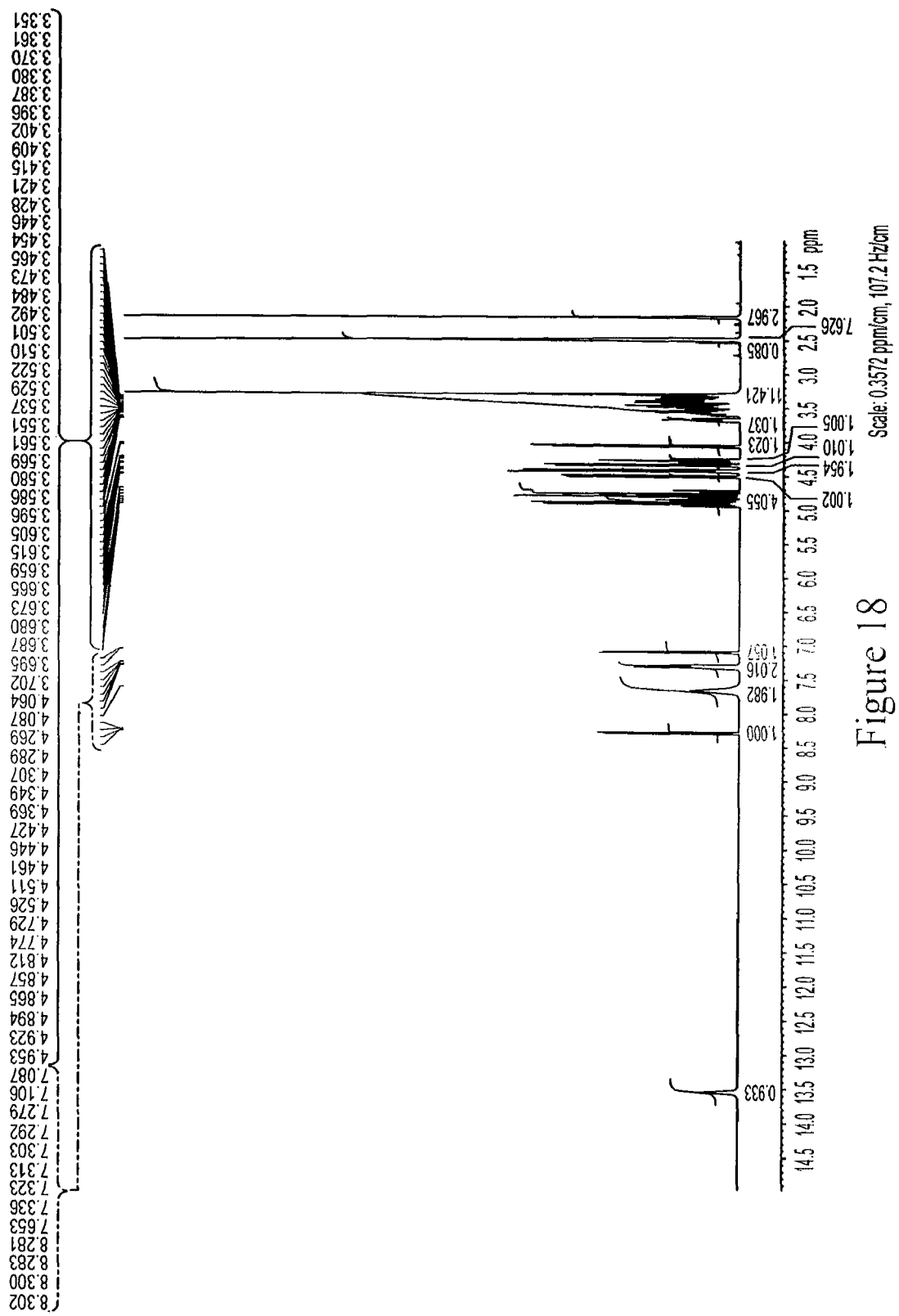
FIG. 18 is $^1$H-NMR spectrum of the 1:1 dexlansoprazole-sorbitol co-crystal of SP134-SBT-P22.
Figure 19:
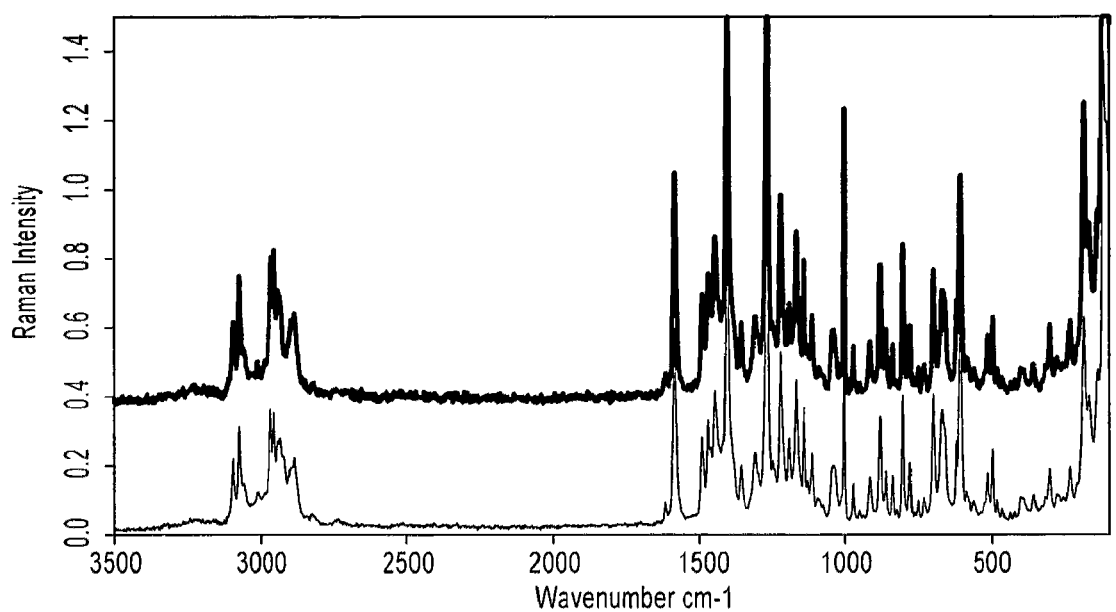
FIG. 19 is FT-Raman spectrum of SP134-SBT-P22 (top) compared to the reference spectrum of 1:1 dexlansoprazole-sorbitol co-crystal (bottom). The spectra have been scaled and offset in the y-direction for purposes of comparison.
Figure 20:
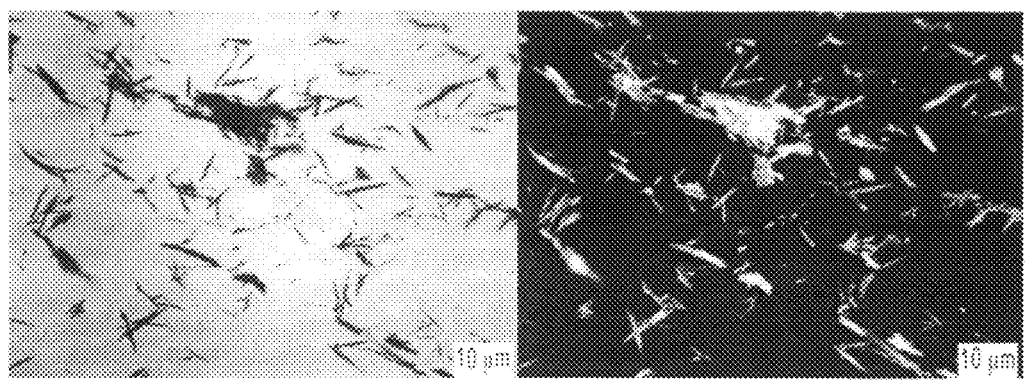
FIG. 20 shows optical microscopy images of SP134-SBT-P22 without (left) and with (right) crossed polarizers.

After drying under vacuum at room temperature a product yield of ~72% was obtained. The material was characterized by $^1$H-NMR (FIG. 18), FT Raman (FIG. 19), PXRD, optical microscopy (FIG. 20), TG-FTIR and HPLC. A 1:1 dexlansoprazole-sorbitol co-crystal was obtained. The PXRD corresponds to the reference SP134-SBT-P24, which could be indexed as pure phase. Analyzed by TG-FTIR, the material contains 0.16% water. The HPLC purity was estimated to be 100.0 area-% (main peak with retention time of 14.9 minutes).

The spontaneous crystallization indicates that the initial concentration of the solution was in the labile region. Even though the crystallization occurred spontaneously, the 1:1 co-crystal was crystallized as a pure phase.

Experiment SP134-SBT-P23

In the second crystallization experiment an initial co-crystal concentration similar to the approximate solubility of the co-crystal (initial conc. 50 mg/mL, approximate solubility 50-63 mg/mL) was used. Sorbitol was suspended in EtOH/DMSO (3:1) at room temperature and heated to 40° C. Care was taken that all material was dissolved and a clear solution was obtained. Dexlansoprazole was also dissolved in EtOH/DMSO (3:1) at room temperature and slowly added at 40° C. to the sorbitol-solution in the contrast to the previous experiment, no spontaneous precipitation occurred, the solution remained clear. The solution was cooled down with a cooling rate of 0.1 K/min to 10° C. and stirred for several hours at 10° C. At the end of the experiment no precipitation was observed.

Experiment SP134-SBT-P24

In order to optimize the starting concentration and the yield, the initial co-crystal concentration was set to 35 mg/mL slightly above the approximate solubility of the co-crystal at 40° C. (17-23 mg/mL), sorbitol was suspended in the EtOH/DMSO (5:1) at r.t. and heated to 40° C. Dexlansoprazole was dissolved in the EtOH/DMSO (5:1) at room temperature and slowly added at 40° C. to the sorbitol-solution. Selected data recorded in-situ with the FBRM probe show that all material was dissolved and a clear solution was obtained. The seed crystals were added at 40° C. and the particle count increased rapidly. The suspension was stirred for 5 min at 40° C. before the cooling (rate: 0.1 K/min) was started. At 40° C. the particle count of the smaller particles (1-5 µm) remained constant, while the count of the larger particles (100-251 µm) and the total number of particles (1-1000 µm) decreased. This effect is most likely due to a grinding of the larger particles which is in equilibrium with a partial redissolving in a not saturated solution, thus a further improvement of the volume efficiency seems possible. As the solubility decreases with decreasing temperature, the saturation limit is reached and at ~38.5° C. and the particle count of the larger particles (10-251 µm) started to increase. At ~29° C. the particle count of the smaller particles increased, at the same time the number of larger particles decreased. This might be due to a breaking and grinding of larger particles into smaller ones. Particle growth (increase in number of larger particles) is observed as the temperatures reaches 10° C. The suspension was cooled down with a cooling rate of 0.1 K/min to 10° C. and stirred at 10° C. for about 10 h.

Figure 21:
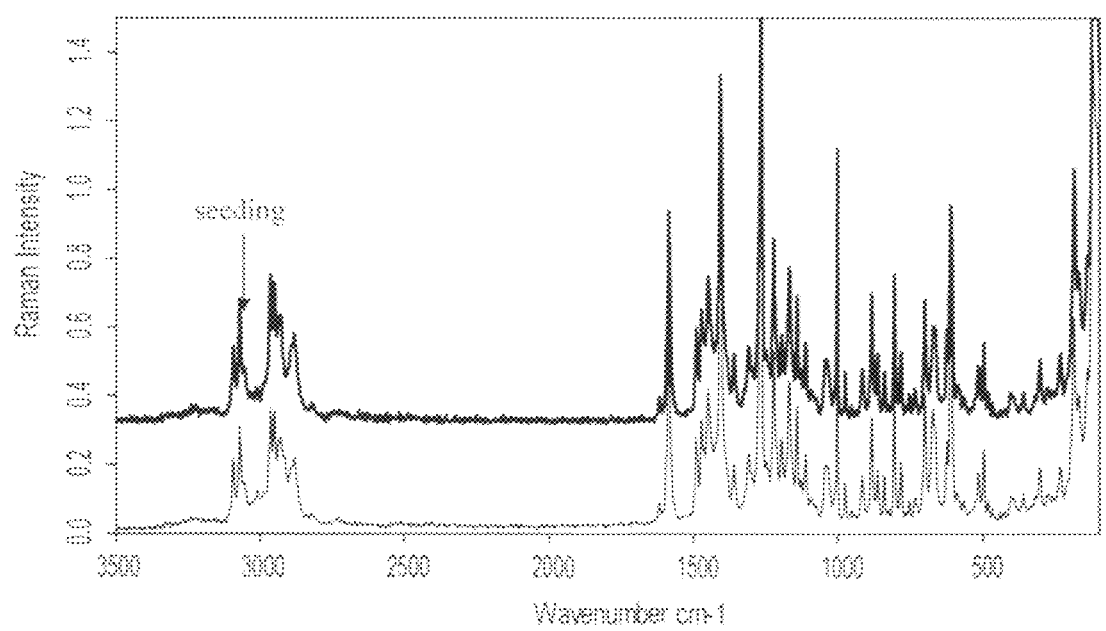
FIG. 21 is FT-Raman spectrum of SP134-SBT-P24 (top) compared to the reference spectrum of 1:1 dexlansoprazole-sorbitol co-crystal (bottom). The spectra have been scaled and offset in the y-direction for purposes of comparison.
Figure 23:
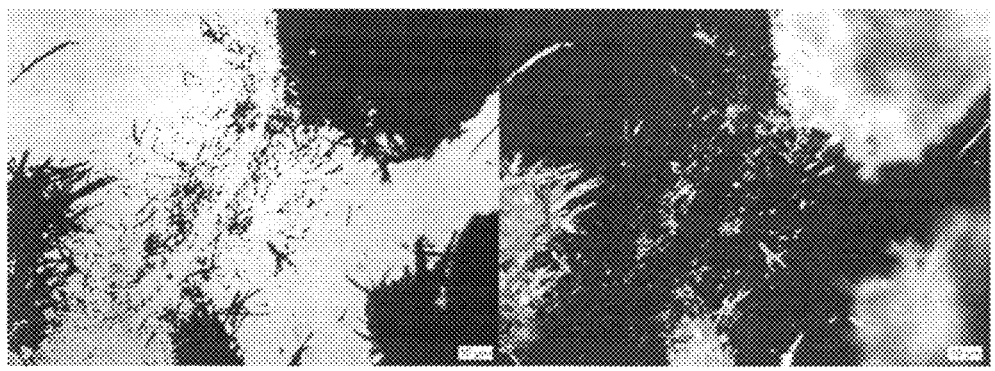
FIG. 23 is optical microscopy images of SP134-SBT-P24 (1:1 dexlansoprazole-sorbitol co-crystal) without (left) and with (right) crossed polarizers.

After drying under vacuum at room temperature a product yield of ~64% was obtained. The material was characterized by FT Raman (FIG. 21), PXRD (FIG. 22), optical microscopy (FIG. 23). TG-FTIR and HPLC. The PXRD could be indexed as pure phase. Analyzed by TG-FTIR, the material contains 0.1% water and 0.7% ethanol. The HPLC purity was estimated to be 100.0 area-% (main peak with retention time of 14.9 minutes).

Experiment SP134-SBT-P25

In order to optimize the starting concentration and the yield, the initial co-crystal concentration was set to 52 mg/mL i.e. 50% increase compared to the previous experiment SP134-SBT-P24. Sorbitol was suspended in EtOH/DMSO (5:1) at room temperature and heated to 40° C. Dexlansoprazole was dissolved in EtOH/DMSO (5:1) at room temperature and slowly added at 40° C. to the sorbitol-solution. Selected data recorded in-situ with the FBRM probe show that all material was dissolved and a clear solution was obtained. The seed crystals were added at 40° C. and the particle count increased rapidly. The suspension was stirred for 5 min at 40° C. before the cooling (rate: 0.1 K/min) was started. At 40° C. the particle count of the smaller (1-5 µm) particles decreased slightly, while the count of the larger particles (100-251 µm) and the total number of particles (1-1000 µm) increased. This effect is most likely due to a growing of the particles. As the solubility decreased with decreasing temperature the particle count of the smaller particles (1-5 µm) started to increase and at ~38-39° C. This effect is most likely due to nucleation and grinding of the larger particles respectively. The suspension was cooled down with a cooling rate of 0.1 K/min to 10° C. and stirred at 10° C. for about 11 h.

Figure 24:
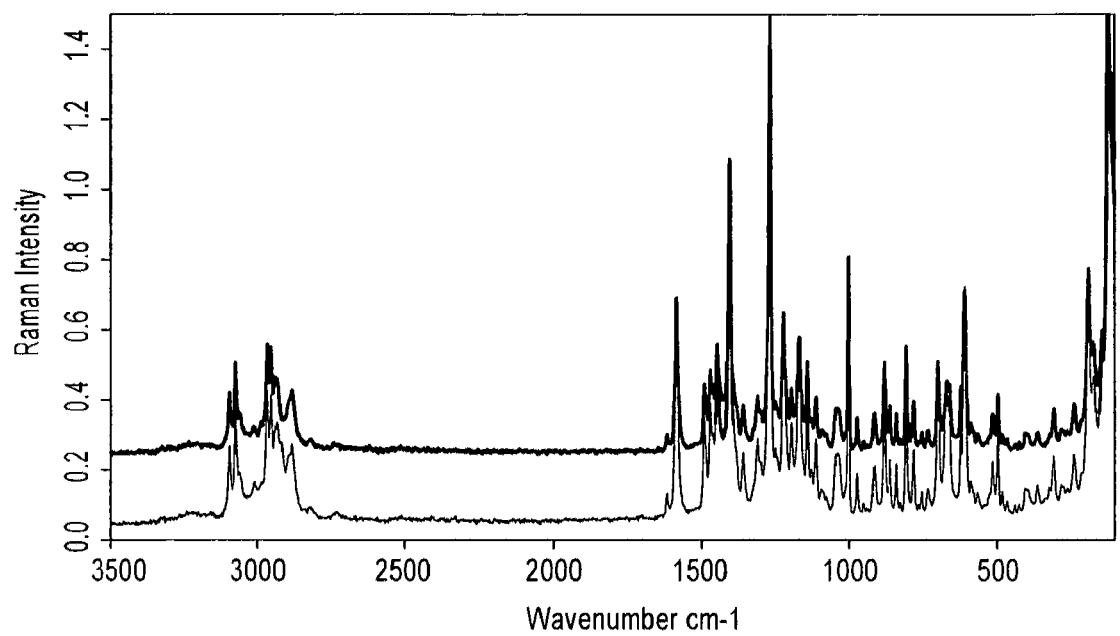
FIG. 24 is FT-Raman spectrum of SP134-SBT-P25 (top) compared to the reference spectrum of 1:1 dexlansoprazole-sorbitol co-crystal (bottom). The spectra have been scaled and offset in the y-direction for purposes of comparison.
Figure 25:
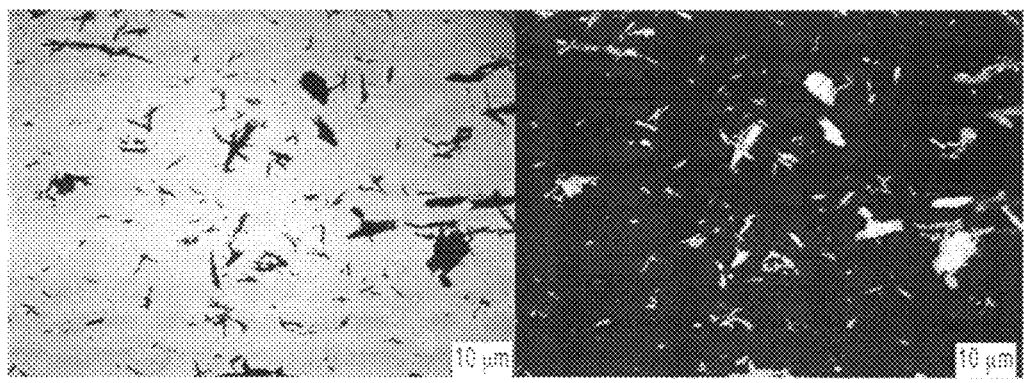
FIG. 25 is optical microscopy images of SP134-SBT-P25 (1:1 dexlansoprazole-sorbitol co-crystal) without (left) and with (right) crossed polarizers.
Figure 26:
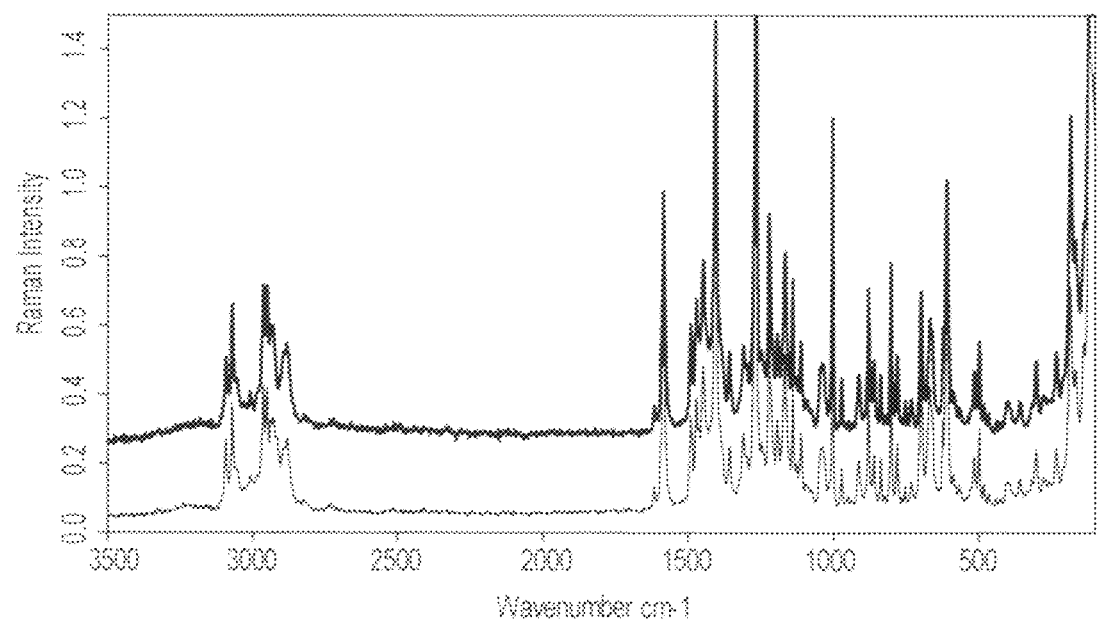
FIG. 26 is FT-Raman spectrum of SP134-SBT-P26 (top) compared to the reference spectrum of 1:1 dexlansoprazole-sorbitol co-crystal (bottom). The spectra have been scaled and offset in the y-direction for purposes of comparison.

After drying under vacuum at room temperature a product yield of ~65% was obtained. The material was characterized by FT Raman (FIG. 24), PXRD, optical microscopy (FIG. 25) and TG-FTIR. The PXRD corresponds to the reference SP134-SBT-P24, which could be indexed as pure phase. Analyzed by TG-FTIR, the material contains 0.07% water.

Experiment SP134-SBT-P26

In order to optimize the starting concentration and the yield, the initial co-crystal concentration was set to 68 mg/mL i.e. 50% increase compared to the previous experiment SP134-SBT-P25 and 100% increase compared to SP134-SBT-P24. Sorbitol was suspended in EtOH/DMSO (5:1) at room temperature and heated to 40-50° C. The clear solution was cooled to the crystallization start temperature of 40° C. Dexlansoprazole was dissolved in EtOH/DMSO (5:1) at room temperature and slowly added at 40° C. to the sorbitol-solution. Selected data recorded in-situ with the FBRM probe show that all material was dissolved and a clear solution was obtained. The seed crystals were added at 40° C. and the particle count increased rapidly. The suspension was stirred for 5 min at 40° C. before the cooling (rate: 0.1 K/min) was started. At 40° C. growing and also nucleation was observed. The particle count of the smaller particles (1-5 µm), of the larger particles (100-251 µm) and of the total number of particles (1-1000 µm) increased. The suspension was cooled down with a cooling rate of 0.1 K/min to 10° C. and stirred at 10° C. for about 8 h. Repeatedly it could be observed that at a specific concentration the count of the larger particles decreased. In parallel the total amount of particles and the amount of the smaller particles increased. This effect is most likely due to grinding of the larger particles.

Figure 27:
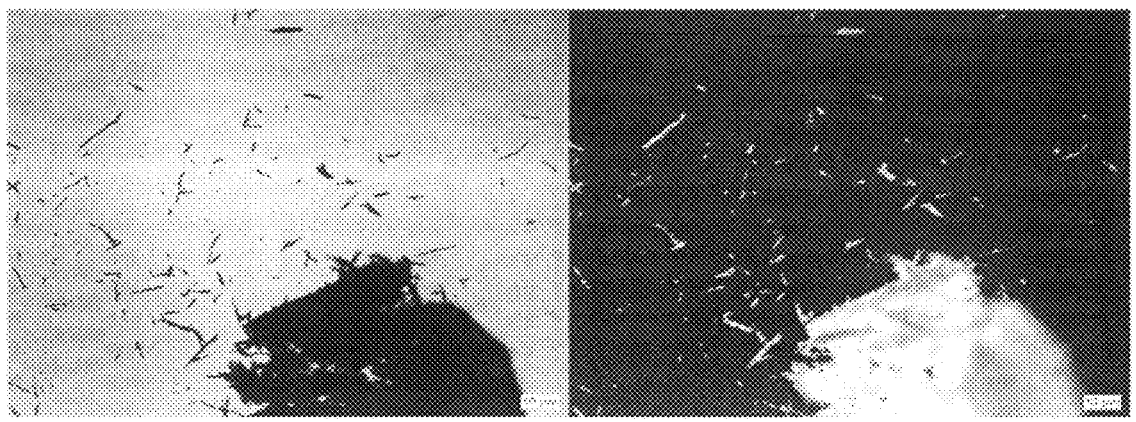
FIG. 27 is optical microscopy images of SP134-SBT-P26 (1:1 dexlansoprazole-sorbitol co-crystal) without (left) and with (right) crossed polarizers.
Figure 28:
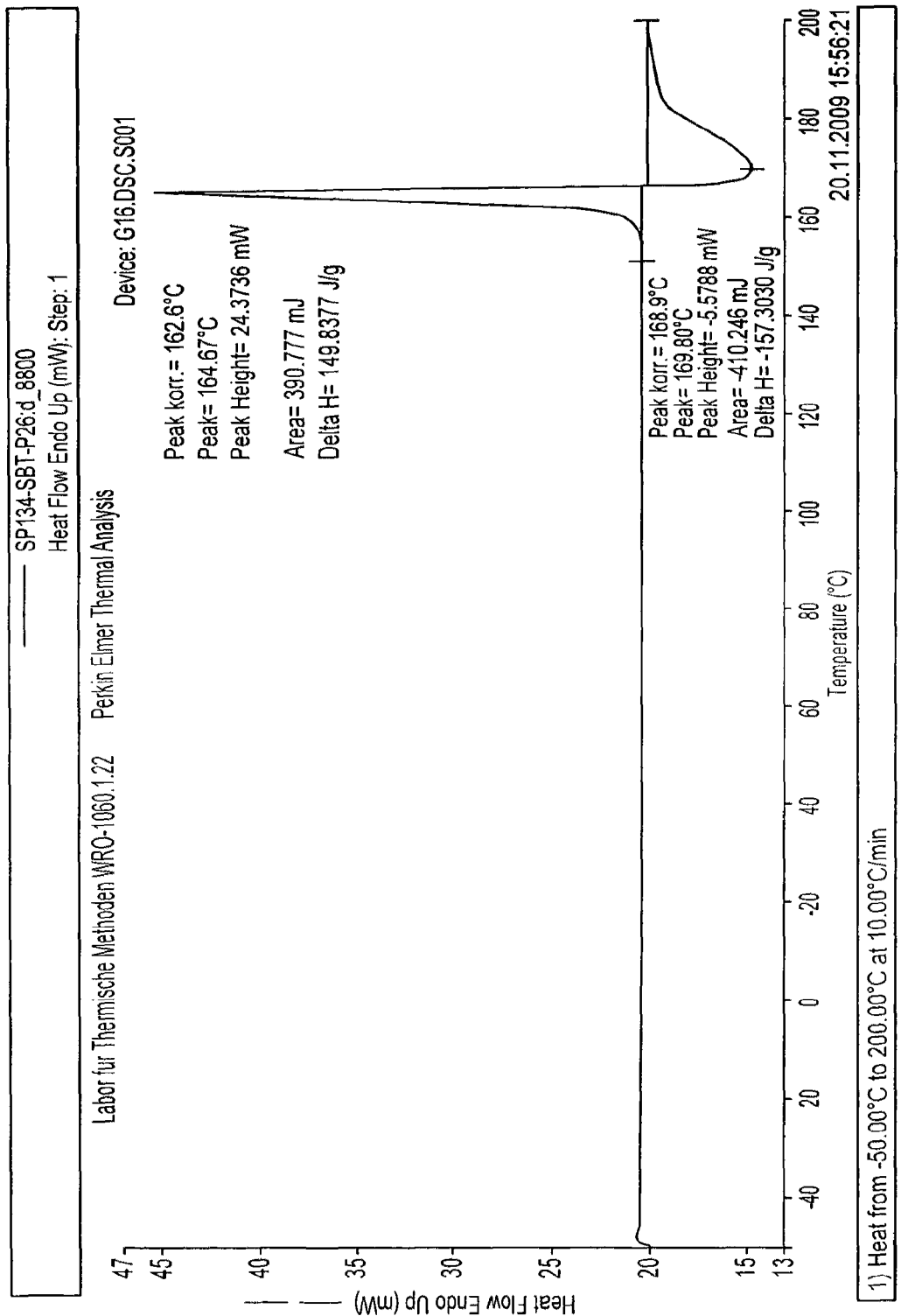
FIG. 28 is a plot of a DSC of sample SP134-SBT-P26 (1:1 dexlansoprazole-sorbitol co-crystal).
Figure 29:
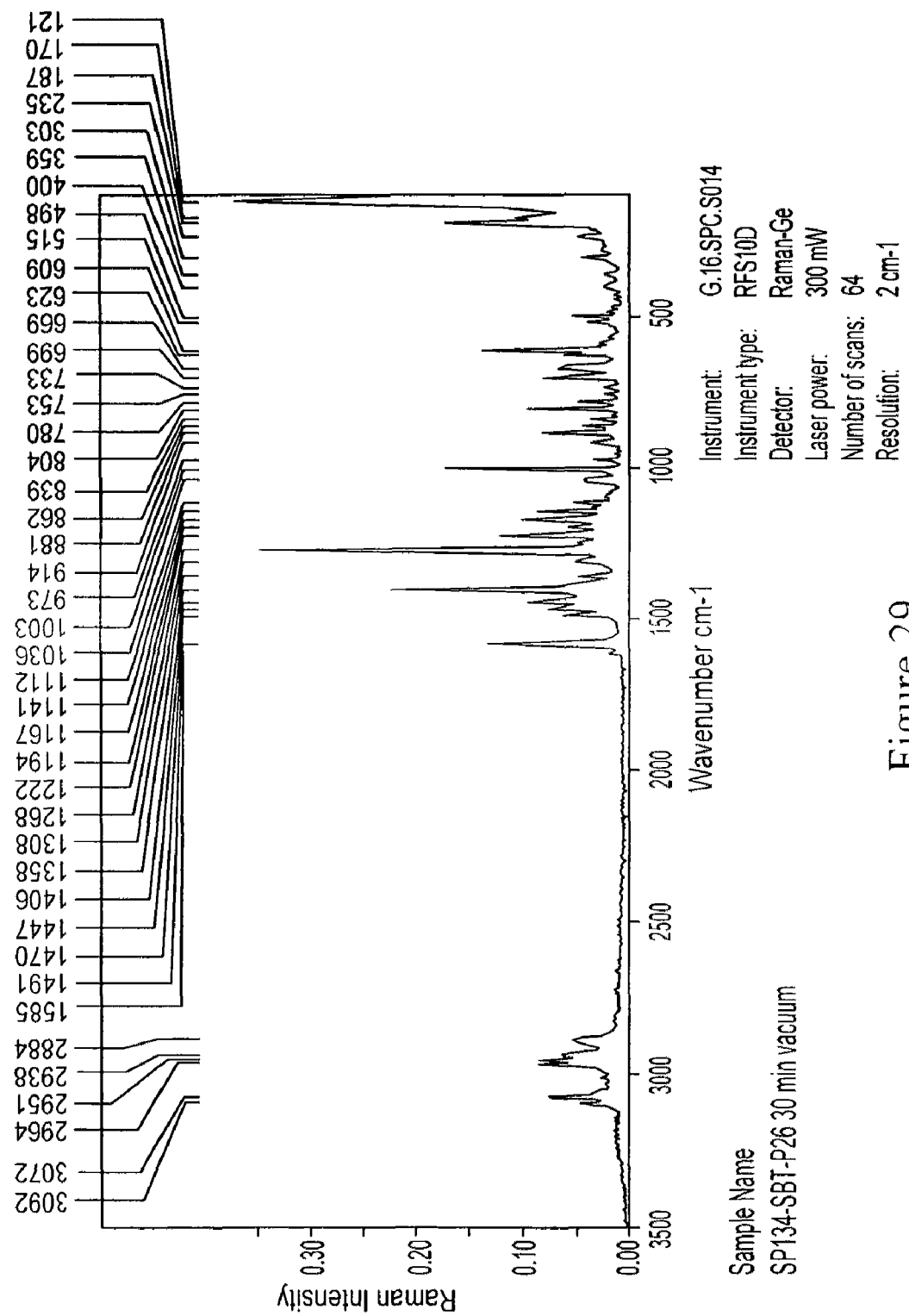
FIG. 29 is a plot of an FT-Raman of the sorbitol co-crystal of the sample SP134-SBT-P26 (1:1 dexlansoprazole-sorbitol co-crystal).
Figure 30A:
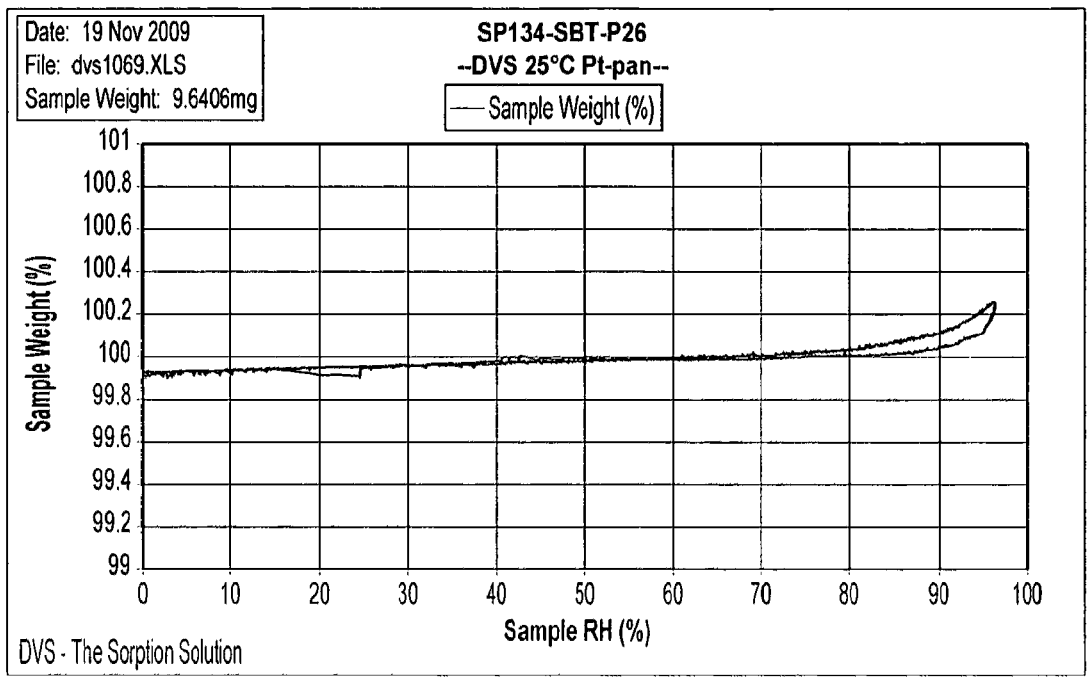
FIG. 30a is DVS curve of SP134-SBT-P26 (1:1 dexlansoprazole-sorbitol co-crystal) with sample weight [%] plotted versus relative humidity.
Figure 30B:
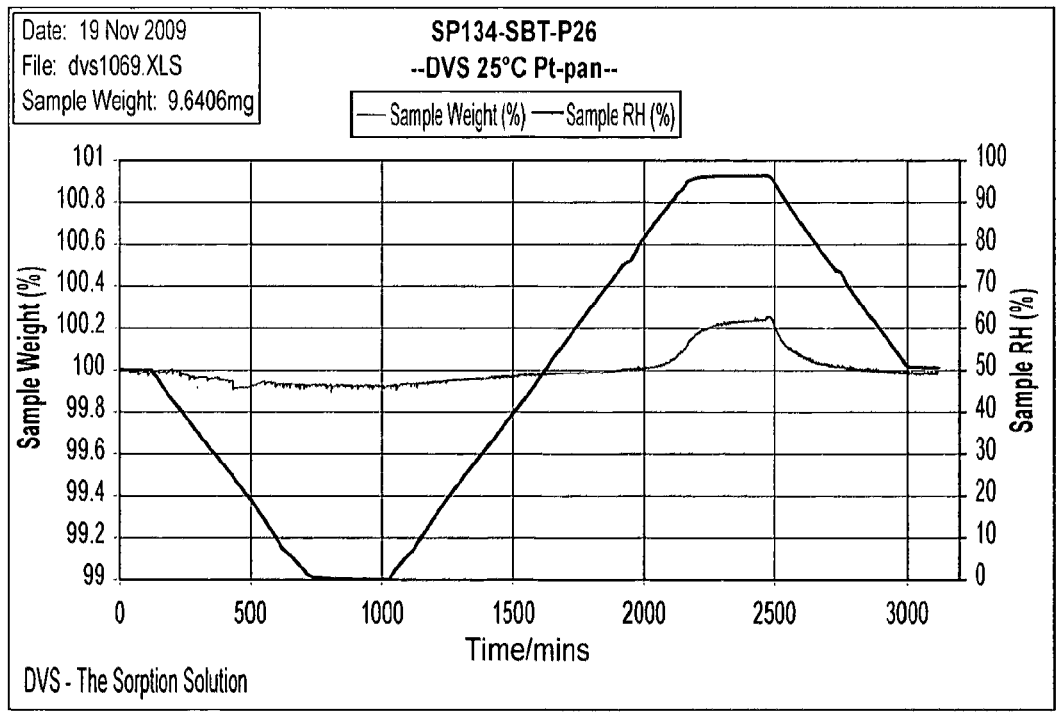
FIG. 30b is DVS curve of SP134-SBT-P26 (1:1 dexlansoprazole-sorbitol co-crystal) with relative humidity and sample weight [%] plotted versus time. Curve near midline: sample weight [%]; S-shaped curve: relative humidity [%].
Figure 31:
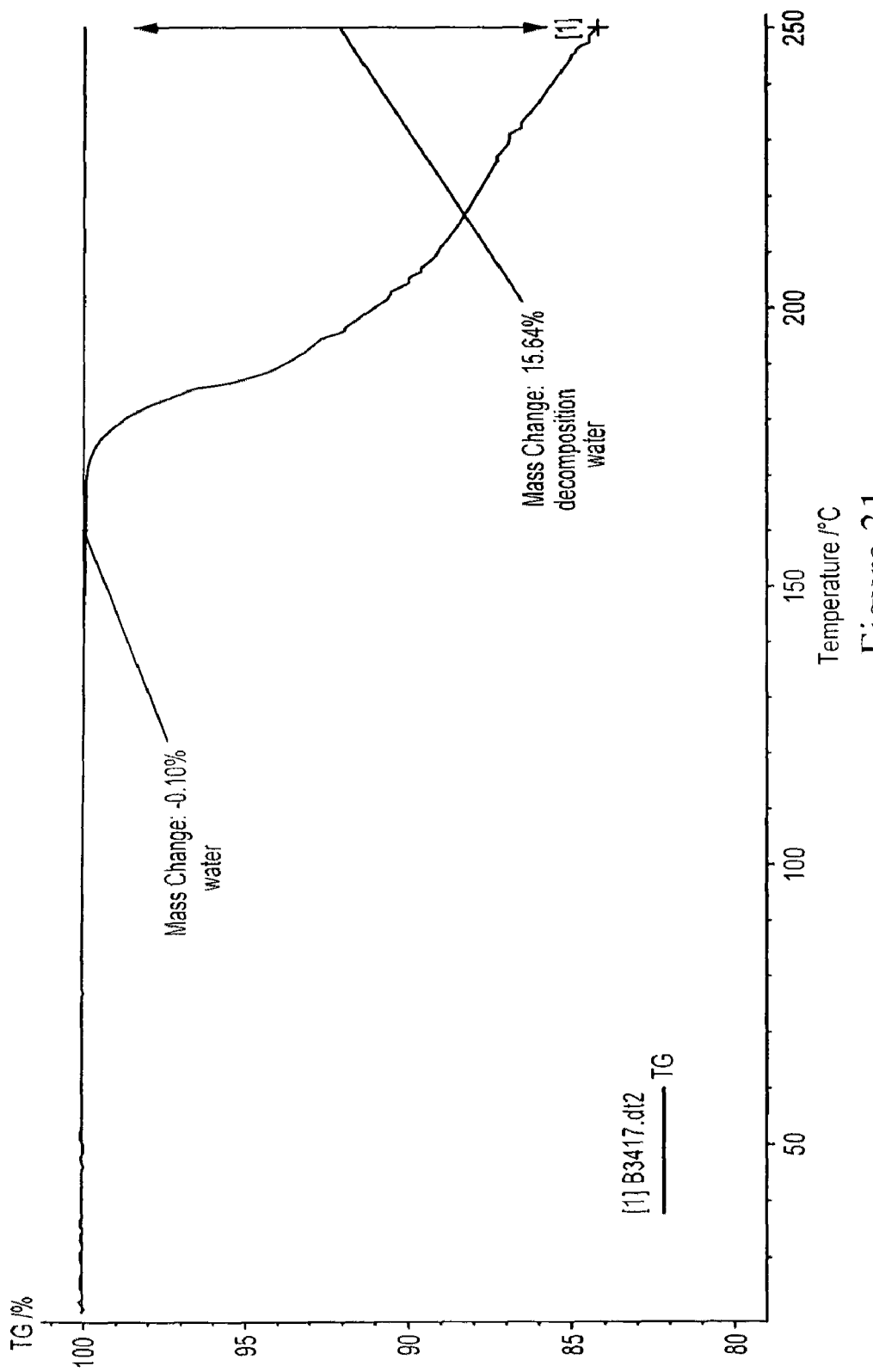
FIG. 31 is a plot of a TG-FTIR of sample SP134-SBT-P26 (1:1 dexlansoprazole-sorbitol co-crystal).

The material was dried under vacuum for about 5 h at 40° C. and afterwards overnight under vacuum at room temperature. A product yield of ~83% was obtained. The solid was characterized by PXRD, optical microscopy (FIG. 27), Karl Fischer, HPLC, DSC (FIG. 28), FT-Raman (FIG. 29), DVS (FIGS. 30a and 30b), and TG-FTIR (FIG. 31). The PXRD corresponds to the reference SP134-SBT-P24, which could be indexed as pure phase. Analyzed by TG-FTIR, the material contains 0.1% water. The water content, determined by Karl Fischer, was <0.05% m/m. The HPLC purity was estimated to be 100.0 area-% (main peak with retention time of 15.0 minutes).

In order to examine the behavior of SP134-SBT-P26 in the presence of variable water vapor pressure, the sample was analyzed by isothermal DVS at 25° C. The resulting DVS curve with the sample weight [%] plotted against the relative humidity over the sample is shown in FIG. 30a. FIG. 30b shows the relative humidity and the sample weight [%] versus time plot. The sample was conditioned at 50% r.h. before starting a pre-defined humidity program with a scanning rate of 5% r.h. change per hour. Below 50% r.h. a small but continuous mass loss of the sample is observed (~0.07%). This mass loss is in good accordance to the results of the TG-FTIR-measurement and Karl Fischer water content determination. The sample shows a small continuous water uptake in the second part of the cycle (0% r.h. up to 95% r.h.). At about 85% r.h. the sample shows a water uptake of 0.12% relative to the mass at 0% r.h. which classifies the sample is not hygroscopic. The sample was checked by FT-Raman (pre- and post DVS measurements) and the material shows no phase transition.

Experiment SP134-SBT-P27

In order to obtain information about the robustness of the process an increased cooling rate of 0.2 K/min instead of 0.1 K/min was tested. In addition, the suspension was cooled to an end temperature of 2° C. instead of 10° C. to check if a higher yield could be obtained. The initial co-crystal concentration was set at 69 mg/mL (similar to SP134-SBT-P26); sorbitol was suspended in EtOH/DMSO (5:1) at room temperature and heated to 40-50° C. The clear solution was cooled to the crystallization start temperature of 40° C. Dexlansoprazole was dissolved in EtOH/DMSO (5:1) at room temperature and slowly added at 40° C. to the sorbitol-solution. Selected data recorded in-situ with the FBRM probe show that all material was dissolved and a clear solution was obtained. The seed crystals were added at 40° C. and the particle count increased rapidly. The suspension was stirred for 5 min at 40° C. before the faster cooling (rate: 0.2 K/min) was started. At first a growing of the particles and after a few minutes stirring at 40° C. also nucleation was observed. The particle count of the smaller particles (1-5 μm), of the larger particles (100-251 μm) and of the total number of particles (1-1000 μm) increased. The suspension was cooled down with a cooling rate of 0.2 K/min to 2° C. and stirred at 2° C. for about 30 min. During the cooling phase it was observed that at a specific concentration the count of the larger particles decreased. In parallel the total amount of particles and the amount of the smaller particles increased. This effect is most likely due to breaking and grinding of the larger particles.

Figure 32:
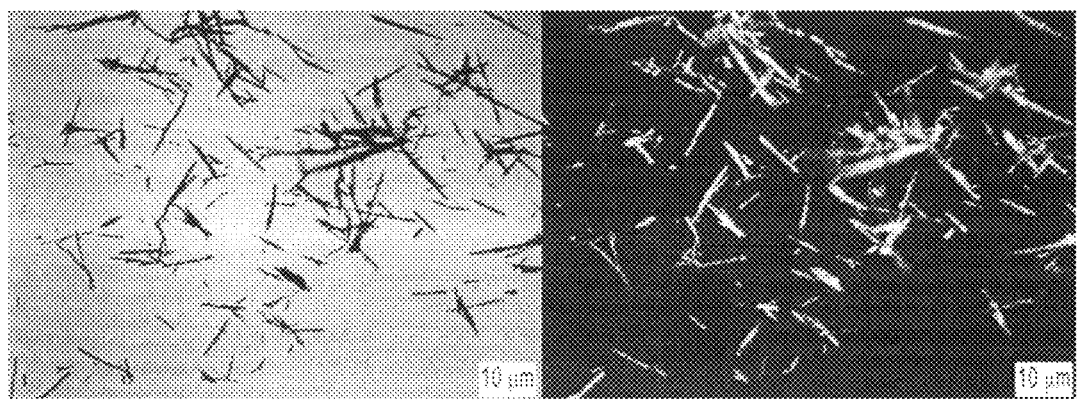
FIG. 32 is optical microscopy images of SP134-SBT-P27 without (left) and with (right) crossed polarizers.

After drying under vacuum at room temperature a product yield of ~78% was obtained. Similar to the yield obtained in SP134-SBT-P26. The material was characterized by FT Raman, PXRD, optical microscopy (FIG. 32), TG-FTIR, HPLC and DVS. The PXRD corresponds to the reference SP134-SBT-P24, which could be indexed as pure phase. Analyzed by TG-FTIR, the material contains 0.07% water. The water content, determined by Karl Fischer, was <0.05% m/m.

The HPLC purity \vas estimated to be 100.0 area-% (main peak with retention time of 14.9 minutes).

In order to examine the behavior of SP134-SBT-P27 in the presence of variable water vapor pressure, the sample was analyzed by isothermal DVS at 25° C. The sample was conditioned at 50% r.h. before starting a pre-defined humidity program with a scanning rate of 5% r.h. change per hour. Below 50% r.h. a small but continuous mass loss of the sample is observed (~0.06%). This mass loss is in good accordance to the results of the TG-FTIR-measurement and Karl Fischer water content determination. The sample shows a small continuous water uptake in the second part of the cycle (0% r.h up to 95% r.h.). At about 85% r.h. the sample shows a water uptake of 0.08% relative to the mass at 0% r.h. which classifies the sample is not hygroscopic. The sample was checked by FT-Raman (pre- and post DVS measurements) and the material shows no phase transition.

Example 3

Summary of Results

The PXRD patterns of both the 1:1 and 1:1.5 dexlansoprazole-sorbitol co-crystals could be indexed, which provides strong evidence for clean co-crystal formation.

Approximate solubilities of the free drug, the co-crystal former and the dexlansoprazole-sorbitol co-crystal were determined in eleven solvents and solvent mixtures.

Slow crystallization experiments with a variety of techniques were carried out, including vapor diffusion, slow cooling, evaporation, and seeding.

Several solvent systems were used, for example EtOAc/DMSO, TBME/DMSO, EtOH/H$_2$O mixtures, pure DMSO, MeOH, and basic, as well as buffered solutions.

The crystalline material obtained was needle- or hair-shaped and not suitable for single crystal X-Ray diffraction.

The PXRD patterns of both the 1:1 and 1:1.5 dexlansoprazole-sorbitol co-crystals were indexed confirming that the patterns correspond to a single form and not to a mixture.

The diffractogram of the 1:1.5 co-crystal can be indexed in the monoclinic space group P2$_1$/c with the conventional unit cell parameters a=4.64 Å; b=30.24 Å; c=19.91 Å; α=γ=90°; β=92.7°.

The diffractogram of the 1:1 co-crystal, prepared as in Example 2, can be indexed in the orthorhombic space group Pba2 with the conventional unit cell parameters a=19.95 Å; b=25.54 Å; c=4.37 Å; α=β=γ=90°.

Characterization of Sorbitol Co-Crystal Material
Preparation and Characterization of the Sorbitol Co-Crystal The 1:1.5 dexlansoprazole-sorbitol co-crystal was prepared on a 500 mg scale as in Example 2 (experiment SP134-SBT-P9) and characterized by FT-Raman spectroscopy, PXRD and $^1$H-NMR. This material was used for the crystallization experiments.

The FT-Raman spectrum and the PXRD pattern correspond well to the spectrum and pattern of the 1:1.5 co-crystal in Example 1. The sample also contains 0.05 mol.-% EtOAc solvent residues.

Approximate Solubility Measurements of the Co-Crystal and its Components

In addition, the approximate solubilities of the dexlansoprazole free drug (SP134-FD-P1), the sorbitol co-crystal former and the co-crystal at room temperature in several different solvents and solvent mixtures were estimated by manual dilution combined with visual observation (see Table 13). The solubility values presented are intended to be regarded as rough estimates and are to be used solely for the design of crystallization experiments. All solvent mixtures are listed as ratios by volume (v/v).

TABLE 13

| Solvent | Solubility (mg/mL) | | |
|---|---|---|---|
| | SP134-FD-P1 | Sorbitol | SP134-SB-P8/-P9 |
| $H_2O$ | <1 | >200 | $0.25^a$ |
| Ethanol | >200 | — | — |
| MeOH | >200 | ~13 | 23-3 |
| EtOAc | >20 | <1 | <1 |
| DMSO | >200 | >200 | — |
| 9:1 EtOAc/DMSO | >200 | ~1 | ~10 |
| 1:1 EtOAc/DMSO | >200 | 125-250 | >200 |
| 1:1 EtOH/$H_2O$ | ~30 | ~160 | $50-100^a$ |
| 2:1 EtOH/$H_2O$ + 5 vol.-% $NH_3$ solution | 100-200 | 125-250 | 60-100 |
| 2:1 MeOH/$H_2O$ + 5 vol.-% $NH_3$ solution | 100-200 | >250 | 60-100 |
| 2:1 MeOH/borax buffer (pH = 9.0)$^b$ | 90-190 | >250 | $45-65^a$ |

$^a$not stable, turns brown after a short while
$^b$FN 73214

Crystallization Experiments

Slow crystallization experiments with a variety of techniques were carried out (SC-XRD, Table 14). The following methods were used: vapor diffusion, cooling crystallization, evaporation and seeding.

In a vapor diffusion experiment a volatile antisolvent diffuses very slowly through the gas phase into a solution of the free drug leading to a slow build up of saturation, followed by supersaturation and possible crystallization.

In cooling crystallization, very slow (e.g., rate of 0.5K/h) cooling of a hot solution close to saturation is used to slowly increase the saturation level until supersaturation is reached leading possibly to crystallization and crystal growth.

In evaporation, slow, partial evaporation builds up saturation, followed by supersaturation and possibly crystallization.

In seeding, the addition of crystalline seed to a supersaturated solution might provide surfaces for further crystal growth.

In addition, six samples of selected solubility measurements were being stored at 4° C. for up to two months to induce crystallization and possible single crystal growth of the dexlansoprazole-sorbitol co-crystal. In several samples a white solid has precipitated or formed at the side walls and was included in the analysis.

The obtained solid material was analyzed by visual observation and some samples were examined by polarizing light microscopy.

TABLE 14

| Experiment | Method | Solvent (Antisolvent) | Conditions | Result |
|---|---|---|---|---|
| -SBT-P10 | vapor diffusion | 9:1 EtOAc/ DMSO (EtOAC) | r.t., 2 w | no precipitation |
| -SBT-P10a | evaporation | 9:1 EtOAc/ DMSO (EtOAC) | r.t., 2 d | white solid at walls |
| -SBT-P10b | seeded evap. | 9:1 EtOAc/ DMSO (EtOAC) | + seeds, 6 d | white solid at walls |
| -SBT-P11 | vapor diffusion | 6:1 TBME/ DMSO (TBME) | r.t., 2 w | no precipitation |
| -SBT-P11a | evaporation | DMSO only | r.t., 7 d | thin white layer at walls |

TABLE 14-continued

| Experiment | Method | Solvent (Antisolvent) | Conditions | Result |
|---|---|---|---|---|
| -SBT-P12 | cooling | 9:1 EtOAc/ DMSO | 70 → 5° C., 0.5 K/h | solution turns black |
| -SBT-P13 | cooling | 2:1 EtOH/$H_2O$ + 5% $NH_3$ | 70 → 5° C., 0.5 K/h | solution turns black |
| -SBT-P14 | cooling | 9:1 EtOAc/ DMSO | 35 → 5° C., 0.5 K/h, resting 3 d | no precipitation |
| -SBT-P14a | evaporation | 9:1 EtOAc/ DMSO | 5° C., 6 d | no precipitation |
| -SBT-P14b | seeding of sat. sol. | EtOAc/DMSO | + seeds, 6 d at 5° C. | no growth |
| -SBT-P15 | cooling | 2:1 EtOH/$H_2O$ + 5% $NH_3$ | 25 → 5° C., 0.5K/h, | only few & small particles |
| -SBT-P15a | resting at 5° C. | 2:1 EtOH/$H_2O$ + 5% $NH_3$ | rest at 5° C., 19 d | white precipitate |
| -SBT-P8-L2 | approx. solubility | MeOH | rest at 5° C., 28 d | white solid at walls |
| -SBT-P9-L7 | approx. solubility | 2:1 EtOH/$H_2O$ + $NH_3$ | rest at 5° C., 26 d | white precipitate |

Figure 33:
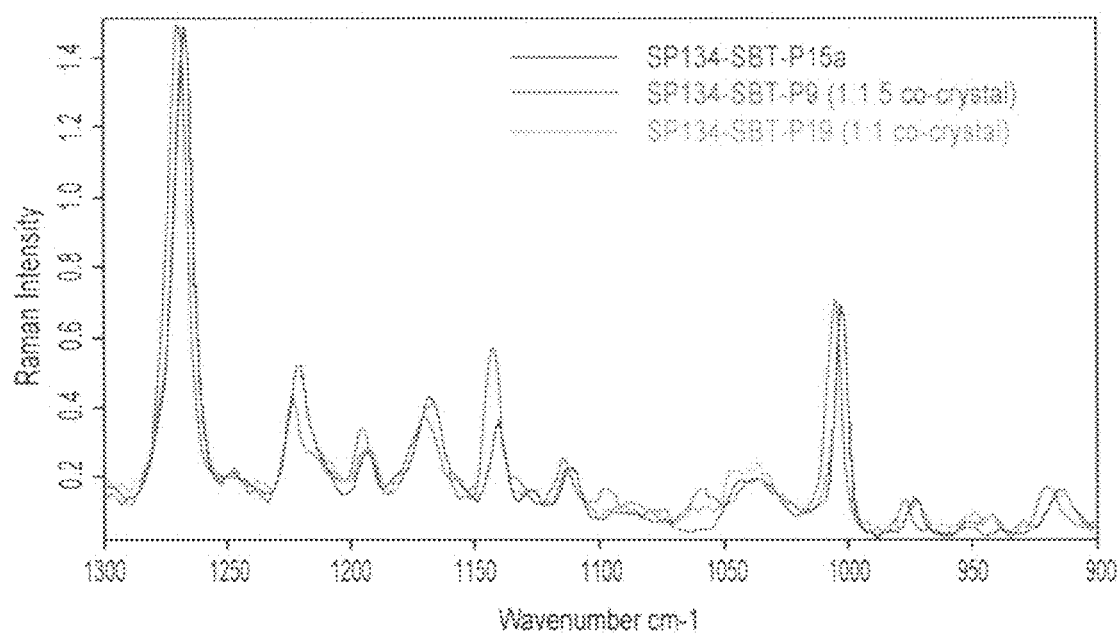
FIG. 33: Detail of FT-Raman spectra (1300-900 cm-1-) of the solid material from experiment SP134-SBT-P15a (blue), of the 1:1.5 co-crystal SP134-SBT-P9 starting material (red), and of the 1:1 co-crystal SP134-SBT-P19 (green) prepared as in Example 2. The spectra have been scaled for purposes of comparison.

The solid material obtained in experiment SP134-SBT-P15a was examined by FT-Raman spectroscopy (FIG. 33). It was found to correspond to the 1:1 dexlansoprazole-sorbitol co-crystal (sample SP134-SBT-P19, prepared as in Example 2) rather than to the 1:1.5 dexlansoprazole-sorbitol co-crystal starting material (sample SP134-SBT-P9).

Indexing of Powder X-Ray Diffractograms

The powder X-ray diffractograms (PXRD) of both the 1:1 co-crystal and the 1:1.5 co-crystal was successfully indexed.

For the 1:1.5 co-crystal the pattern of sample SP134-SBT-P9 and for the 1:1 co-crystal the pattern of sample SP134-SBT-P24 were indexed using DICVOL91 within the X'Pert HighScore Plus program package. A summary of the obtained parameters is given in Table 15.

The diffractogram of the 1:1.5 co-crystal sample SP134-SBT-P9 can be indexed in the monoclinic space group $P2_1/c$. The low Rp values of the Le-Bail fit show a good agreement with the experimental data. This confirms that the pattern of the 1:1.5 dexlansoprazole-sorbitol co-crystal corresponds to a single form and not to a mixture.

For the 1:1 co-crystal, the sample SP134-SBT-P24 can be indexed in the orthorhombic space group Pba2. Here, the low Rp values of the Le-Bail fit also show a good agreement with the experimental data. This confirms that also the pattern of the 1:1 dexlansoprazole-sorbitol co-crystal corresponds to a single form and not to a mixture.

TABLE 15

Parameters of indexed XRPD patterns.

| | 1:1.5 co-crystal SP134-SBT-P9 (file: J190) | 1:1 co-crystal SP134-SBT-P24 (file: J467) |
|---|---|---|
| Space Group | P21/c | Pba2 |
| Volume of unit cell conventional | 2792 A3 | 2226 A3 |
| unit cell parameters | | |
| a | 4.64 A | 19.95 A |
| b | 30.24 A | 25.54 A |
| c | 19.91 A | 4.37 A |
| α | 90.0° | 90.0° |
| β | 92.7° | 90.0° |
| γ | 90.0° | 90.0° |

TABLE 15-continued

Parameters of indexed XRPD patterns.

| | 1:1.5 co-crystal<br>SP134-SBT-P9<br>(file: J190) | 1:1 co-crystal<br>SP134-SBT-P24<br>(file: J467) |
|---|---|---|
| $R_p$ | 5.39% | 5.91% |
| weighted $R_p$ | 7.57% | 8.20% |

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description is offered by way of illustration only and not as a limitation.

What is claimed is:

1. A crystal comprising: dexlansoprazole and sorbitol, wherein the crystal is a co-crystal or a salt thereof of dexlansoprazole and sorbitol and is substantially crystalline in structure.

2. The crystal of claim 1, wherein the dexlansoprazole and the sorbitol are present at about a 1:1 molar ratio.

3. The crystal of claim 1, wherein the dexlansoprazole and the sorbitol are present at about a 1:1.5 molar ratio.

4. The crystal of claim 1, wherein the crystal has a differential scanning calorimetry (DSC) pattern substantially as set forth in FIG. 12 or FIG. 28.

5. The crystal of claim 1, wherein the crystal has a dynamic vapor sorption (DVS) pattern substantially as set forth in FIG. 13, FIG. 30a or FIG. 30b.

6. The crystal of claim 1, wherein the crystal has an X-ray powder diffraction (XRPD) pattern substantially as set forth in FIG. 15 or FIG. 22.

7. The crystal of claim 1, wherein the crystal has a Raman spectrum substantially as set forth in FIG. 14 or FIG. 29.

8. The crystal of claim 1, wherein the crystal has an $^1$H-NMR spectrum substantially as set forth in FIG. 10 or FIG. 18.

9. The crystal of claim 1, wherein the dexlansoprazole and the sorbitol are at least about 90 mole percent of the crystal.

10. A method for making a co-crystal or salt thereof, comprising the steps of:
a) mixing dexlansoprazole and sorbitol in an amount of one or more solvents effective to yield a substantially homogeneously dispersed solution and
b) evaporating the one or more solvents from the solution.

11. The method of claim 10, wherein the dexlansoprazole and the sorbitol are mixed in about a 1:1 molar ratio or about a 1:1.5 molar ratio.

12. The method of claim 10, wherein the solution is evaporated under nitrogen.

13. The method of claim 10, wherein the solution is evaporated at an ambient temperature.

14. The method of claim 10, wherein the solution is mechanically agitated for at least about 24 hours after mixing and prior to evaporation of the solvent.

15. A method for making a co-crystal or salt thereof, comprising the steps of:
a) dissolving sorbitol in one or more solvents to form a sorbitol solution;
b) adjusting temperature of the sorbitol solution to about 40° C.;
c) dissolving dexlansoprazole in one or more solvents to form a dexlansoprazole solution;
d) adding the dexlansoprazole solution to the sorbitol solution to form a mixture at a temperature ranging from about 40° C. to about 45° C.;
e) cooling the mixture to a temperature ranging from about 2° C. to about 10° C.;
f) stirring the mixture at a temperature ranging from about 2° C. to about 10° C. for a period of time ranging from about 30 minutes to about 25 hours; and
g) recovering the co-crystal or salt thereof which precipitates from the mixture in step (f).

16. The method of claim 15, wherein the one or more solvents comprise ethanol (EtOH), DMSO, ethyl acetate (EtOAc), tetrahydrofuran (THF), acrylonitrile (MeCN), acetonitrile, methanol (MeOH), tert-butyl methyl ether (TBME) or combination thereof.

17. The method of claim 15, wherein the one or more solvents comprise DMSO/EtOH (1:5, v/v).

18. The method of claim 15, wherein step (e) is carried out at a cooling rate ranging from about 0.1 K/min to about 0.2 K/min.

19. The method of claim 15, wherein seeding crystals in a suspension are added to the mixture before step (e).

20. The method of claim 15, wherein the co-crystal or salt thereof is recovered by vacuum filtration in step (g).

21. The method of claim 15, wherein step (a) is carried out at an ambient temperature.

22. The method of claim 15, wherein step (a) is carried out at an ambient temperature followed by heating to a temperature ranging from about 40° C. to about 60° C.

23. The method of claim 15, wherein step (c) is carried out before or concurrently with step (b) or step (a).

* * * * *